United States Patent [19]

Wu et al.

[11] Patent Number: 5,452,723

[45] Date of Patent: Sep. 26, 1995

[54] CALIBRATED SPECTROGRAPHIC IMAGING

[75] Inventors: Jun Wu, Cambridge; Michael S. Feld, Waban, both of Mass.; Richard P. Rava, Palo Alto, Calif.; Firooz Partovi, Brookline, Mass.

[73] Assignee: Massachusetts Institute of Technology, Cambridge, Mass.

[21] Appl. No.: 920,135

[22] Filed: Jul. 24, 1992

[51] Int. Cl.$^6$ .................................................. A61B 6/00
[52] U.S. Cl. .................... 128/664; 128/665; 250/339.01; 250/340; 356/318; 356/326
[58] Field of Search ..................................... 128/633, 664, 128/665, 634; 250/338.1, 340, 301, 339.01; 356/300, 326, 317, 318

[56] References Cited

U.S. PATENT DOCUMENTS

| Re. 31,815 | 1/1985 | Alfano | 128/665 |
|---|---|---|---|
| 4,162,405 | 7/1979 | Chance et al. | 250/461 |
| 4,178,917 | 12/1979 | Shapiro | 128/665 |
| 4,194,217 | 3/1980 | Bosch | 358/93 |
| 4,236,526 | 12/1980 | Richard | 128/663 |
| 4,336,809 | 6/1982 | Clark | 128/665 |
| 4,556,057 | 12/1985 | Hiruma et al. | 128/303 |
| 4,569,354 | 2/1986 | Shapiro et al. | 128/665 |
| 4,597,392 | 7/1986 | Optiz et al. | 128/637 |
| 4,641,650 | 2/1987 | Mok | 128/303 |
| 4,737,628 | 4/1988 | Lovoi | 250/226 |
| 4,768,513 | 9/1988 | Suzuki | 128/665 |
| 4,773,097 | 9/1988 | Suzaki et al. | 128/665 |
| 4,930,516 | 6/1990 | Alfano et al. | 128/663 |
| 4,957,114 | 9/1990 | Wu et al. | 128/665 |
| 4,981,138 | 1/1991 | Deckelbaum et al. | 128/665 |
| 5,003,977 | 4/1991 | Suzuki et al. | 128/633 |
| 5,042,494 | 8/1991 | Alfano | 128/665 |
| 5,046,501 | 9/1991 | Crilly | 128/665 |
| 5,062,428 | 11/1991 | Chance | 128/664 |
| 5,062,431 | 11/1991 | Potter | 128/665 |
| 5,088,492 | 2/1992 | Takayama et al. | 128/654 |
| 5,104,392 | 4/1992 | Kittrell et al. | 606/15 |
| 5,119,815 | 6/1992 | Chance | 128/633 |

FOREIGN PATENT DOCUMENTS

| 929-050 | 4/1978 | U.S.S.R. |
|---|---|---|
| 2203831 | 10/1988 | United Kingdom |
| WO88/09145 | 12/1988 | WIPO |
| WO90/05563 | 5/1990 | WIPO |

OTHER PUBLICATIONS

Alfano et al. "Laser Induced Flourescence Spectroscopy From Native Cancerous and Normal Tissue" *IEEE Journal of Quantum Electronics* (Dec. 1984) No. 12, pp. 1507–1511.

Montan et al. "Multicolor Imaging and Contrast Enhancement In Cancer-Tumor Localization Using Laser-Inducted Flourescence In Hematoporphrin-Derivative-Bearing Tissue", *Optics Letter* 10(2): pp. 56–58 (Feb. 1985).

Anderson et al. "Tumour Localization By MEans of Laser-Induced Fluorescence in Hematoporphyrin derivative (HPD)-Bearing Tissue" *Laser Spectroscopy VII*, Proceeding os the Seventh International Conference (Jun. 1985) pp. 401–406.

(List continued on next page.)

*Primary Examiner*—Ruth S. Smith
*Attorney, Agent, or Firm*—Hamilton, Brook, Smith & Reynolds

[57] ABSTRACT

The present application is directed to the use of photon migration analysis to provide a method of analyzing the diffuse reflectance, fluorescence, Raman or other types of spectra obtained from tissue. This procedure provides a means for processing spectral data such that the distortion in fluorescence spectra, for example, caused by the interplay of a variety of factors such as scattering, absorption, geometry and boundary conditions, can be precisely removed simply by measuring the diffuse reflectance spectrum as well as a second selected spectrum, such as fluorescence, and adjust the spectrum with the reflectance spectrum as described herein. By this procedure, the sample-to-sample variability is minimized. The intrinsic spectrum extracted by this procedure can be easily deconvoluted and provide quantitative information about the physicochemical composition of tissue. Analytical procedures for clinical diagnosis have been developed based on this method.

22 Claims, 15 Drawing Sheets

OTHER PUBLICATIONS

Richards–Kortum et al. "A Model For extraction of Diagnostic Information From Laser Induced Fluorescence Spectra of Human Artery Wall" *Spcetrochima Acta*, vol. 45A No. 1 pp. 87–93 (1989).

Baraga et al. "Ultraviolet Laser Induced Fluorescence of Human Aorta" *Spectrochimica Acta*, vol. 45A, No. 1, pp. 95–99 (1989).

Sartori et al. "Autofluorescence Maps of Atherosclerotic Human Arteries–A New Technique In Medical Imaging" *IEEE Journal of quantum Electronice vol. QE23, No. 10 pp. 1794–1797 (Oct. 1987)*.

Richards–Kortum, R., et al., "A One–Layer Model of Laser–Induced Fluorescence for Diagnosis of Disease in Human Tissue: Applications to Atherosclerosis," IEEE Transactions on Biomedical Engineering, 36(12):1222–1232, (Dec. 1989).

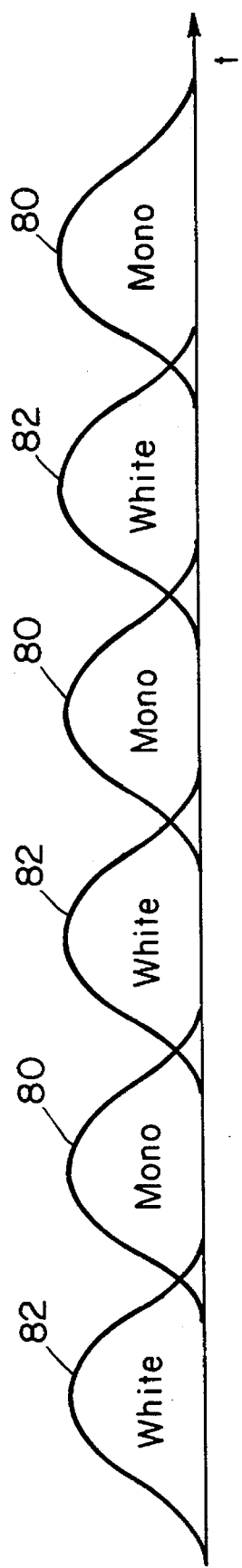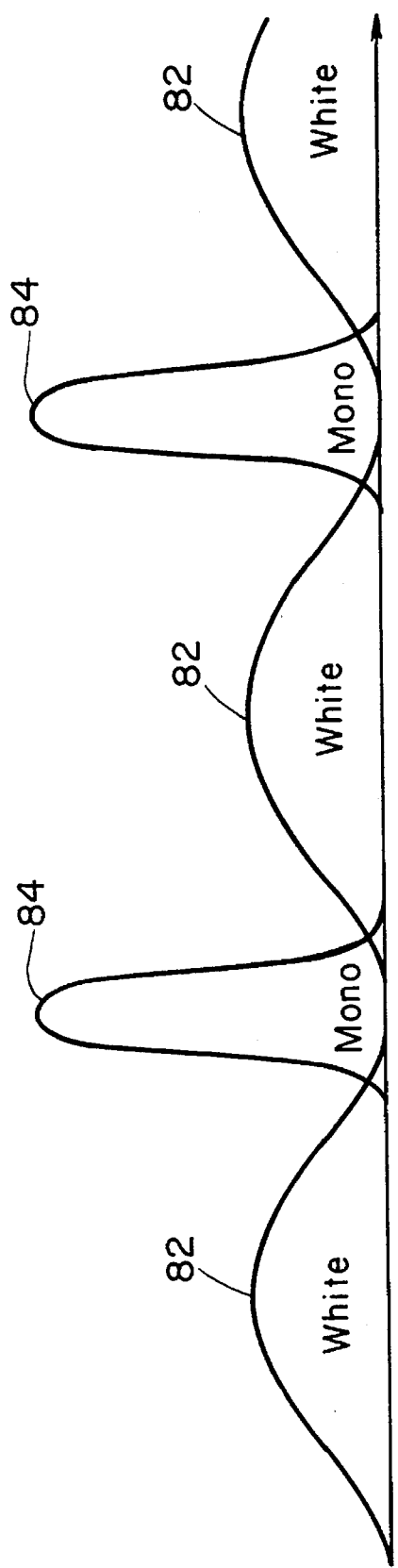

CALIBRATED SPECTROGRAPHIC IMAGING

GOVERNMENT SUPPORT

This invention was made with government support under Grant Number NIH-5-P41-RR02594 awarded by the National Institutes of Health. The Government has certain rights in the invention.

BACKGROUND OF THE INVENTION

Spectroscopy utilizing inelastically scattered light, including fluorescence and Raman spectroscopy, has been explored as a technique for medical diagnosis. Promising results have been reported using tissue autofluorescence and Raman emissions to detect a diversity of diseases, such as occlusions including atherosclerosis in the vascular system including peripheral and coronary arteries, and precancerous or cancerous lesions in colon and bladder wall. Rapid in vivo methods of diagnosis based on fluorescence, Raman, and other spectral analysis methods will provide important diagnostic advances.

A majority of the diagnostic methods employed with inelastically scattered light utilize empirical algorithms derived from studying a limited number of specimens. Such empirical algorithms generally fail to utilize the wealth of biochemical and/or morphological information contained in the tissue spectrum. With fluorescence spectroscopy, for instance, part of the difficulty has been that fluorescence spectra observed from optically thick tissue is distorted from the intrinsic spectra of individual fluorescence fluorophores by the interplay of factors such as scattering, absorption, device geometry and tissue boundary conditions. Thus, experiments utilizing optical fiber probes in the clinical setting will often yield results different from those utilizing a laboratory spectrofluorimeter. In addition, the experimental data also depend on whether the tissue-environment boundary condition is index-matched or index-mismatched. Raman spectroscopy is affected in a similar manner.

A need exists, therefore, for methods of obtaining and analyzing optical information retrieved from tissue under study, both in vitro and in vivo, that provides more complete and uniform characterization of the tissue to aid in diagnosis.

SUMMARY OF THE INVENTION

A method which can remove the distorting effects on the spectroscopic information from inelastically scattered light, including fluorescence spectra, retrieved from optically thick tissues would allow correlation of the clinically obtained in vivo tissue spectra with the fluorophores present within the tissue. Methods which incorporate the effects of the intrinsic fluorescence, scattering, absorption, excitation and collection geometries used for delivery and retrieval of light to and from the tissue, respectively, and the tissue boundary conditions must be developed to move beyond current empirical approaches. Such methods will allow the accurate extraction of the information or the physicochemical composition of the tissue, and thus provide biochemical and morphological information about tissue pathology for tracking the development of disease in vivo.

R. Richards-Kortum et al., "A one layer model of laser-induced fluorescence for diagnosis of disease in human tissue applications to atherosclerosis", IEEE Transactions in Biomedical Engineering 36, 1222–1232 (1989), described a one layer model based on the assumption that light is attenuated exponentially in tissue. They utilized this model to develop a diagnostic procedure which demonstrated effective diagnosis of atherosclerosis in human artery. Unfortunately, this model does not correct for geometric effects. It has been shown that tissue fluorescence can strongly depend on the geometry of excitation and collection thereby requiring additional steps for calibrating the system.

The present application is directed to the use of photon migration analysis to provide a method of analyzing the diffuse reflectance, fluorescence, Raman or other types of spectra obtained from tissue. This procedure provides a means for processing spectral data such that the distortion in fluorescence spectra, for example, caused by the interplay of a variety of factors such as scattering, absorption, geometry and boundary conditions, can be precisely removed simply by measuring the diffuse reflectance spectrum as well as a second selected spectrum, such as fluorescence, and adjust the spectrum with the reflectance spectrum as described herein. By this procedure, the sample-to-sample variability is minimized. The intrinsic spectrum extracted by this procedure can be easily deconvoluted and provide quantitative information about the physicochemical composition of tissue. Analytical procedures for clinical diagnosis have been developed based on this method.

The problem of defining the physical mechanism that accurately describes the spectroscopic properties of human tissue is an issue of understanding the light fluence distribution within a turbid medium. Initially, a collimated beam impinges on the tissue, and can be scattered or absorbed by constituents in the tissue. Scattered photons are generally forward directed in human tissue, and continue, with additional scattering events, until they are absorbed. The excited molecule can either dissipate its energy as heat or re-radiate a fluorescent or Raman scattered photon. In the case of fluorescence spectroscopy molecules which fluoresce act as isotropic point sources of radiation within the tissue. The fluorescence is also scattered and absorbed on its way out of the tissue to the detector.

The large amount of scattering in tissue precludes a simple determination of the functional form of the light fluence distribution. Light propagation in a highly scattering medium is commonly estimated by the radiative transfer equation. Since a general solution is not known, approximations which lead to analytical solutions for estimating scattering media have been considered. So called "Monte Carlo" calculations have been extensively utilized, offering the advantage that complex geometries and inhomogeneities can be modeled.

Recently, photon migration methods have been examined for their ability to explain the light distribution and spectroscopy (diffuse reflectance) in scattering media. In this approach, photons are considered to follow probablistic paths which can be fully described by distribution functions. The method allows analytical solutions to be determined for different boundary conditions, while providing an intuitive picture for the interaction of the photons with the scattering media. In this application, we apply this approach to a semi-infinite scattering slab, and obtain an analytical solution which fully describes the reflectance for the range of scattering, absorption and anisotropy coefficients typically found for human tissue. By introducing a probability distribution function which depends only on the anisotropy coefficient, the phase dependence can be separated from the absorption and scattering coefficients. Such a separation provides both accuracy and simplicity in the diffuse reflectance calculation.

The photon migration picture is extended to model the fluorescence from turbid media such as human tissue. The photon migration approach suggests that the distortion in a fluorescence spectrum caused by the interplay of scattering, absorption, geometry and boundary conditions can be precisely removed by measuring the diffuse reflectance spectrum over the same wavelength range and in the same manner as the fluorescence spectrum, and applying this diffuse reflectance spectrum to the fluorescence spectrum in a well defined manner. The result is the same intrinsic fluorescence spectrum as would be obtained from thin (10 μm) tissue slices which are not distorted by these factors.

This approach also provides a method for analyzing the Raman spectroscopy of tissue, and provides for the extraction of information on tissue composition and for design of fiber optic probes for utilizing these techniques in the clinical setting. Spectral diagnosis systems and methods are more fully described in U.S. Pat. No. 4,913,142 issued to Kittrell, et al.; and pending applications U.S. Ser. No. 07/288,772 filed Dec. 21, 1988 by Kittrell, et al.; and International Application No. PCT/US92/00420 filed Jan. 17, 1992 by Rava, et al, which are incorporated herein by reference. The methods and systems employed herein can be used to diagnose a large variety of diseases, such as cancer and vascular obstructions, wherein the concentration of tissue components correllated with various stages of disease can be determined either relatively or absolutely to provide effective methods of diagnosis. As noted in the above application, the present methods can be used for real time imaging and/or spectral mapping of disease as well as single pixel diagnostics. These diagnostic methods can then be used for direct electronic control of laser surgical systems.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3a and 3b show illumination timing diagrams for alternately illuminating and collecting reflectance and inelastic scattering emissions from a tissue sample with the spectroscopy systems of FIG. 1.

DESCRIPTION OF THE PREFERRED EMBODIMENTS

Figure 1:
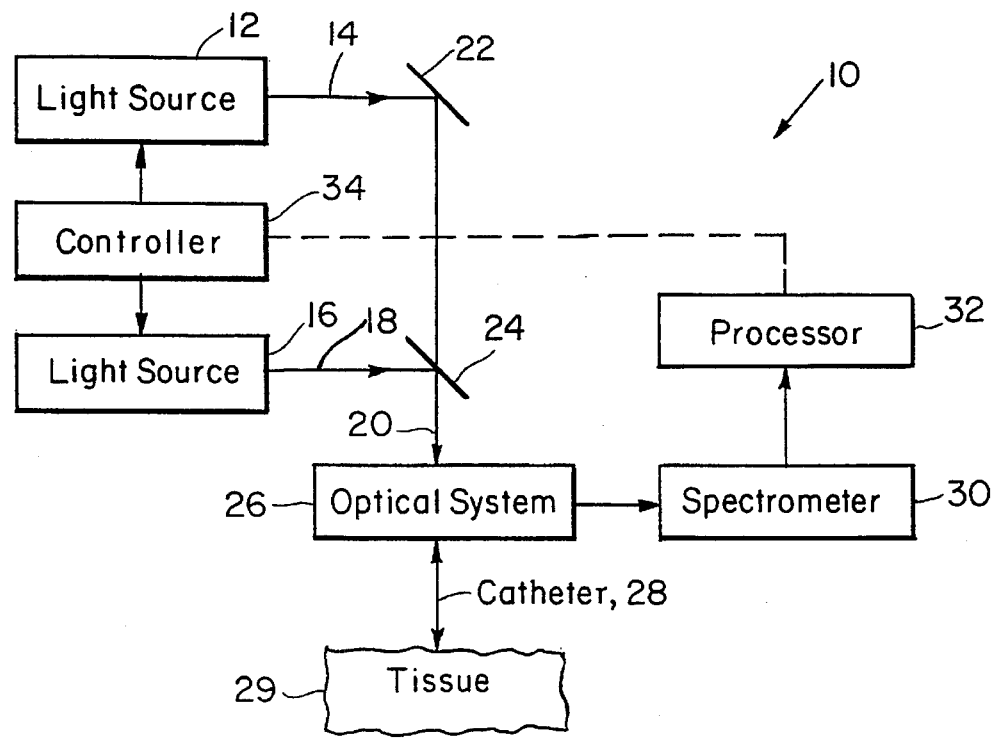
FIG. 1 shows a block diagram of the fluorescence spectroscopy system of this invention which features laser and white light sources.

FIG. 1 shows an embodiment of a fluorescence spectroscopy system 10 of this invention for extracting intrinsic fluorescence from an optically thick turbid media such as human tissue 29. Spectroscopy system 10 allows measurement of the intrinsic fluorescence lineshapes by measuring the bulk fluorescence and diffuse reflectance of the media, and then using the diffuse reflection measurement to correct the bulk fluorescence measurement to obtain the intrinsic fluorescence of the media.

System 10 employs an excitation light source 12 which generates a beam 14 of substantially monochromatic light at a wavelength known to induce inelastic scattering in the media. Light source 12 can be, for instance, a laser or filtered light source producing substantially monochromatic light at the desired excitation wavelength, e.g., 476 nm for fluorescence spectroscopy. The system 10 also employs another light source 16 which generates a beam 18 of light over a band of wavelengths for inducing diffuse reflectance in the media. Light source 16 can be, for instance, a white light source or scanned laser light source producing light over the band of desired reflectance wavelengths, e.g, 450–650 nm for the fluorescence spectroscopy example described herein.

The beams 14 and 18 can be directed along a single path 20 by mirrors 22 and 24, respectively. The beams can then be delivered into optical system 26 for coupling to a fiber optic catheter 28, or another optical delivery system.

Spectroscopy system 10 also employs a spectrometer 30 which is optically coupled to optical system 26 for collecting the fluorescence and diffuse reflectance emissions returned through fiber optic catheter 28. The output of spectrometer 30 is coupled to processor 32 for processing in accordance with this invention to produce the intrinsic fluorescence spectrum. A controller 34 alternately illuminates the sample with either light beam 14 or light beam 18 so that spectrometer 30 can collect bulk fluorescence and diffuse reflectance emissions from the turbid media, respectively.

Figure 2:
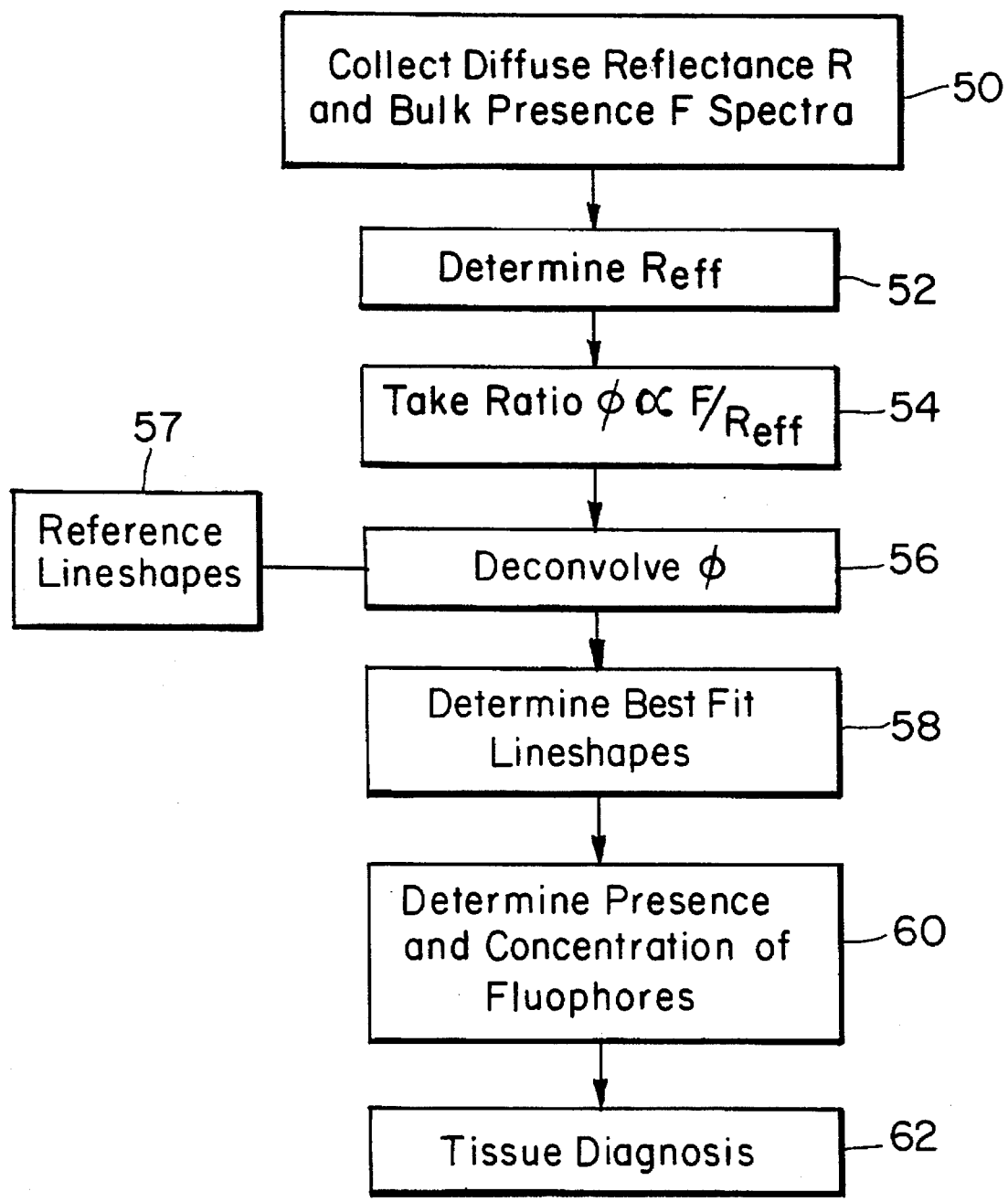
FIG. 2 shows a flowchart of a method for diagnosing tissue using the fluorescence spectroscopy system of FIG. 1 and the spectral enhancement techniques of this invention.

FIG. 2 shows a flowchart of a preferred method for extracting diagnostic information from optically thick turbid tissue using the techniques of this invention. The diffuse reflectance R and the bulk fluorescence F spectra are collected 50 from the tissue being analyzed. Collection of the R and F spectra can be accomplished using the spectroscope 10 of FIG. 1.

Next, the effective diffuse reflectance spectrum $R_{eff}$, which is the reflectance spectrum adjusted for index matched boundary conditions, is determined 52 in accordance with this invention from the collected reflectance spectrum R.

The intrinsic fluorescence spectrum $\phi$ is then determined 54 in accordance with this invention by dividing the bulk fluorescence spectrum F by the effective reflectance spectrum $R_{eff}$.

The intrinsic fluorescence spectrum $\phi$ is then deconvoluted 56 with a set of reference fluorophoric lineshapes 57 to determine a best fit match 58 between the lineshapes and $\phi$. The best fit match is then analyzed 60 to determine the presence and concentration of the reference fluorophores. The tissue is then diagnosed 62 based on the fluorophore presence and concentration information.

FIGS. 3a and 3b show examples of illumination timing diagrams for controlling light sources 12 and 16 of spectroscopy system 10 (FIG. 1). FIG. 3a shows the case where each of the light sources 12 and 16 alternately illuminate the tissue with monochromatic light pulses 80 from light source 12 and white light pulses 82 from light source 16. Each of the pulses illuminates the sample tissue for approximately the same amount of time with approximately the same amount of energy. The diffuse reflectance measurements are accumulated during the white light illumination periods 82, while the bulk fluorescence measurements are accumulated over the monochromatic illumination periods 80.

FIG. 3b shows the case where light source 12 is for example, a high power pulsed laser issuing high energy output pulse 84 of short duration. In this case, white light illumination periods 82, having relatively low energy, are alternated with the high energy monochromatic light pulses 84. The diffuse reflectance and bulk fluorescence measurements are again accumulated over multiple illumination periods. Note that the diffuse reflectance emission can typically be 100–1000 times greater than the fluorescence emission from the tissue for the same illumination energy. Therefore, using high energy monochromatic pulses and accumulating the fluorescence emissions over multiple pulses can be used to increase bulk fluorescence spectral signals well above the noise floor. By decreasing the amount of white light, methods for processing the resulting tissue spectra also permit excitation by both sources at the same time. Readily available signal processing systems can be used to discriminate between the recorded fluorescence and reflectance spectra to provide for the determination of the intrinsic fluorescence as outlined herein.

Note further that scanning excitation systems such as tunable lasers or scanning monochromators can also be employed in measuring the reflectance or inelastically scattered light or both.

Figure 4:
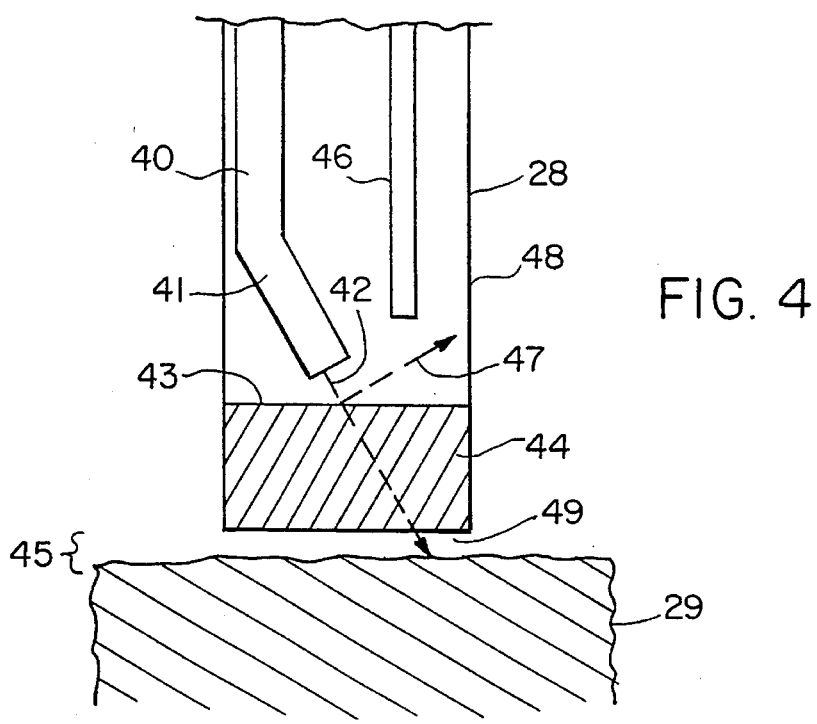
FIG. 4 shows an endoscopic optical fiber catheter for reducing specular reflections and used with the spectroscopy system of FIG. 1.

FIG. 4 shows a preferred embodiment of a fiber optic catheter or endoscope 28 for reducing unwanted specular reflections from tissue sample 29 for making diffuse reflectance measurements. Catheter 28 includes a delivery optical fiber 40 for illuminating the tissue sample 29 with either light beam 14 or 18 from light source 12 or 16, respectively (FIG. 1). The end 41 of optical fiber 40 is bent at an acute angle so that the incident light beam 42 from the fiber impinges on an optically smooth surface 43 of an optical coupling medium 44. Optical coupling medium 44 is index-matched to the tissue 29 so that little or no specular reflection occurs of the interface 45 between the catheter 28 and tissue 29. Catheter 28 also includes a collection optical fiber or fiber bundle 46 for collecting the induced emissions from tissue sample 29. The collection fiber optics 46 can be positioned at the same angle of incidence as the delivery fiber optics 41. Delivery optical fiber 40 is angled so that specular reflections 47 from surface 43 are directed toward the side 48 of catheter 28 where they are absorbed, without being directed into collection catheter 46.

Catheter 28 can be used in contact or non-contact modes with tissue 29. In contact mode, the end of catheter 28 is placed in direct contact with tissue 29 to accomplish index-matched optical coupling. Non-contact mode can be desirable for reducing motion induced artifacts. In the non-contact mode, the gap 49 left between the end of catheter 28 and tissue 29 can be filled with an index-matched fluid to prevent specular reflections.

Where the fiber optics 41, 46 deliver and collect radiation from a known volume of tissue, absolute measurements of the concentration of tissue components can be made using the methods outlined in greater detail below.

DIFFUSE REFLECTION ANALYSIS

In order to calculate the diffuse reflectance from a semi-infinite slab of tissue, a probability distribution function that a photon will escape from the tissue after n scattering events, $f_n(g)$, is introduced. This approach allows separation of the phase dependence of scattering, described by the anisotropy coefficient, g, from the absorption, $\mu_a$, and scatter, $\mu_s$, coefficients in the calculation of diffuse reflectance. It can be demonstrated that $f_n(g)$ and g are related to each other via a universal probability function. The analytical form of this probability function is explored and used to obtain the diffuse reflectance from tissue. The diffuse reflectance calculated with this method is in excellent agreement with Monte Carlo simulations over the parameter range typically found in human tissue, even for the values in which diffusion theory is a poor approximation.

Tissue optical properties are generally specified by three quantities: 1) the absorption coefficient, which is the probability of a photon being absorbed per unit pathlength; 2) the scattering coefficient, $\mu_a$, which is the probability of a photon being scattered per unit pathlength; and 3) the phase function, $p(\Theta)$, which describes the scattering angular distribution, where $\Theta$ is the angle of photon deflection after a single scattering event. The first moment of this phase function, g, is the average cosine of the scattering angle. Various studies have indicated that with visible light sources, the range of the optical parameters in different human tissues (aorta, bladder, brain, liver, skin, lung and muscle) is 0.1 mm$^{-1}$<$\mu_a$<2.0 mm$^{-1}$, 3.0 mm$^{-1}$<$\mu_s$<50 mm$^{-1}$, and 0.68<g<0.96. The measurement analyzed ratio of scattering to absorption, $\mu_s/\mu_a$, in the range from 5 to 300 (essentially the entire range of interest for human tissue), and the anisotropy g in the range from 0.7 to 0.95. The index of refraction of the tissue relative to the surrounding medium can also be important. Both index-matched and non-index-matched boundary conditions are considered. In the next two sections the Monte Carlo and diffusion theory methods are briefly reviewed which are utilized in this application for comparison to the photon migration theory presented in subsequent sections.

Monte Carlo Method

The Monte Carlo method performs by recording individual photon histories in a straightforward manner. In this approach, a photon injected into tissue is allowed to travel freely for approximately one mean free path based on the tissue parameters before it interacts with a tissue particle. Upon interaction, the photon is either absorbed, or scattered. If scattered, it travels in a new direction determined by the phase function. For a semi-infinite slab of tissue, the process is allowed to continue until either the photon is absorbed, or the photon is re-emitted out of the tissue.

In order to simulate this process, the Monte Carlo method uses a random number generator to sample random variables, such as the path length between two interaction events, the occurrence of absorption, and the scattering angle. The values of these variables are chosen randomly from their probability distributions. In the simulations presented here, the following three probability distribution functions are utilized:

1. The probability of moving a path length, L, is determined by the sum of the absorption and scattering coefficients, $\mu_t=\mu_s+\mu_a$ where $\mu_t$ is defined as the total extinction coefficient. Using Beer's law, the probability distribution function of the path length, p(L), is given by:

$$p(L) = \eta_t \exp(-\mu_t L) \quad (1)$$

2. The probability of a photon being absorbed, p(A), upon interaction with a tissue particle depends on both the absorption and the scattering coefficients, and is given by:

$$p(A) = \frac{\mu_a}{\mu_a + \mu_s} \quad (2)$$

3. The deflection angle in a single scattering event is determined by the Henyey-Greenstein phase function, which is known to provide a particularly good representation of the scattering in tissue:

$$p(\theta,\phi) = \frac{1}{4\pi} \frac{(1-g^2)}{(1+g^2-2g\cos\theta)^{3/2}} \quad (3)$$

Using a large number of photons, the Monte Carlo method allows a statistically precise result to be obtained. Therefore, it serves as a reliable standard to test the accuracy of other models. The Monte Carlo programs utilized for this analysis showed agreement with standard results. In this discussion, all simulations utilized 100,000 photons unless otherwise noted.

Diffusion Theory

Since the general solution of the radiative transfer equation is not known, diffusion theory is widely used in modeling the light distribution in human tissue. The primary assumption of diffusion theory is that a diffuse intensity is strongly and approximately uniformly scattered in all directions. Thus, the angular distribution of the scattering can be approximated by the first two terms of the Legendre polynomial expansion. In the case of a collimated beam with intensity $F_0$ incident on a semi-infinite slab of tissue, the average diffuse intensity at depth z, $U_d(z)$, is given by:

$$U_d(Z) = C \exp(-\mu_t Z) + C_2 \exp(-\kappa_d Z) \quad (4)$$

where:

$$C = -\frac{Q_o}{\mu_t^2 - \kappa_d^2}$$

$$C_2 = -\frac{C(1+\mu_t h)}{(1+\kappa_d h)} - \frac{Q_1}{2\pi(1+\kappa_d h)}$$

$$Q_o = \frac{(3\mu_s\mu_{tr} + 3\mu_s\mu_t g)}{4\pi} F_0$$

$$Q_1 = \frac{\mu_s g}{\mu_{tr}} F_o$$

$$\mu_t = \mu_s + \mu_a$$

$$\mu_{tr} = (1-g)\mu_s + \mu_a$$

$$\kappa_d = \sqrt{3\mu_a(\mu_a + (1-g)\mu_s)}$$

$$h = \frac{2}{3\mu_{tr}}$$

The diffuse flux at the tissue surface (z=0) can be calculated from:

$$F_d(Z) = \frac{\mu_s g}{\mu_{tr}} F_o \exp0(-\mu_t Z) - \frac{4\pi}{3\mu_{tr}} \frac{d}{dZ} U_d(Z) \quad (5)$$

Thus, the diffuse reflectance, in the $-z$ direction, is defined as the ratio of the diffuse flux at the surface the incident intensity. The diffusion theory result is:

$$R = -\frac{\mu_s g}{\mu_{tr}} - \frac{4\pi}{3\mu_{tr}} (C\mu_t + C_2\kappa_d) \quad (6)$$

Since diffusion theory is considered valid only in the regime where the scattering is almost isotropic, and is much stronger than the absorption, it deviates from more accurate calculations when applied to the highly anisotropic scattering media such as tissue. Nonetheless, it is applied in many instances to approximate the tissue properties. Below, eq. (6) is used to compare the results of this analytical approach to photon migration theory and Monte Carlo calculations.

Photon Migration Theory

Because of the large number of photons involved in the interaction of light with tissue, the photon migration process can be considered from a probabilistic point of view. Consider a collimated light beam incident on this semi-infinite homogeneous tissue slab. Initially, a photon is injected into the tissue and travels freely. When the photon interacts with a particle in the tissue, it has certain probability of being absorbed, $\mu_a/(\mu_a+\mu_s)$, and a certain probability of being scattered, $\mu_s/(\mu_a,\lambda_s)$. In the photon migration approach presented herein, the photon is reduced in its "weight" by the probability of absorption at every tissue interaction. The new photon weight is equal to the old weight multiplied by the factor $(1-\mu_a/(\mu_a+\mu_s))=\mu_s/(\mu_a+\mu_s)$. The photon continues in a direction determined by the phase function, until its next interaction within the tissue.

For a semi-infinite slab of tissue which is optically thick, every photon is eventually re-emitted out of tissue, but with a reduced weight reflecting the number of interactions the photon has undergone before leaving the tissue. Emitted photons are observed experimentally as diffuse reflectance. For photon scattered n times before being re-mitted from the tissue, the weight of the photon is given by $a^n$ where $a=\mu_s/(\mu_a+\mu_s)$, the albedo. The probability distribution that a photon will escape from the tissue after n scattering events is labeled $f_n$. This probability distribution is functionally dependent on g, but independent of $\mu_a$ and $\mu_s$ because for a semi-infinite slab the photon path is determined by g only. Thus, the diffuse reflectivity, $R(\mu_a,\mu_s,g)$, the ratio of the total power of diffuse reflected light to the total incident power, is given by:

$$R(\mu_a,\mu_s,g) = \sum_{n=1}^{\infty} a^n f_n(g) \qquad (7)$$

Since in the semi-infinite geometry all photons eventually escape from the tissue surface and are detected, the normalization condition $$\sum_{n=1}^{\infty} f_n(g) = 1 \qquad (8)$$

is required.

In this model, the probability distribution, $f_n(g)$, separates the phase dependence of the scattering from the parameters $\mu_a$ and $\mu_s$. This suggests that $f_n(g)$ can be determined for a given tissue type, but is approximately independent of irradiation wavelength because g is not strong function of wavelength. In the following section, we discuss evaluation of a simplified scattering probability distribution which provides an intuitively useful description of $f_n(g)$.

(1) Simplified Scattering Probability Distribution

A 3-dimensional, fixed free path photon migration is considered in an initial attempt to understand the form of $f_n(g)$. For each scattering event, the photon is allowed to travel in one of six directions, +x, −x, +y, +z and −z, with equal probability. If the photon enters in the +z direction, it will only leave the tissue if it is scattered in the −z direction. Thus, the probability that the photon will leave the surface after a single interaction, $f_1$, is equal to ⅙. After two interactions, there are four possible ways for the photon to be re-emitted, (+x, −z), (−x, −z), (+y, −z) and (−y, −z). Thus, $f_2=4/6^2$. Similarly, other $f_n$'s can be determined. Several examples are:

$$f_1 = \frac{1}{6^1}, f_2 = \frac{4}{6^2}, f_3 = \frac{17}{6^3}, f_4 = \frac{76}{6^4}, f_5 = \frac{354}{6^5}, \qquad (9)$$

$$f_6 = \frac{1988}{6^6}, f_7 = \frac{10821}{6^7}$$

The ratio between any two consecutive terms in eq. (9) is approximately ⅚, indicating that $f_n(g)$ can be approximated as an exponential function. Eq. (8) implies that $f_n(g)$ take the form:

$$f_n(g)=k(g)e^{-k(g)n} \qquad (10)$$

where k is constant which depends on g. The reflectance can now be written and evaluated by replacing the sum in eq.(7) by an integral, changing the lower limit of the integral from one to zero. The result is $$R(\mu_a,\mu_s,g) = \int_0^{\infty} a^n k(g)\, e^{-k(g)n} dn \qquad (11a)$$

$$R(\mu_a,\mu_s,g) = \frac{k(g)}{k(g) - \ln(a)} \qquad (11b)$$

The goal now is to find the relationship between k(g) and g. Since for most tissues $\mu_s$ is much greater than $\mu_a$ in the wavelength ranges of interest (350 nm to nm) we can expand $-\ln(a)$ in eq. (11b) is expanded and higher order terms neglected, such that $-\ln(a)=(\mu_a/\mu_s)$. Therefore, the reflectance can be written as $$R(\mu_a,\mu_s,g) = \frac{k(g)\mu_s}{k(g)\mu_s + \mu_a} \qquad (12)$$

Eq. (12) provides a simplified description of the reflectance, and provides an explanation for the observed experimental relationship between the diffuse reflectance and $\mu_s(1-g)/\mu_a$. This can be seen utilizing the similarity relations in the diffusion domain which state that $\mu_a'=\mu_a$ and $(1-g')\mu_s'=(1-g)\mu_s$, or that different sets of $\mu_a$, $\mu_s$ and g can provide similar estimates of the radiance. The similarity relations are valid for g>0.7. Applied to eq. (12), we find that $$\frac{k(g)}{1-g} = \frac{k(g')}{1-g'} = S \qquad (13)$$

indicating that k(g) should be directly proportional to 1-g where S is the proportionality constant.

Figure 5:
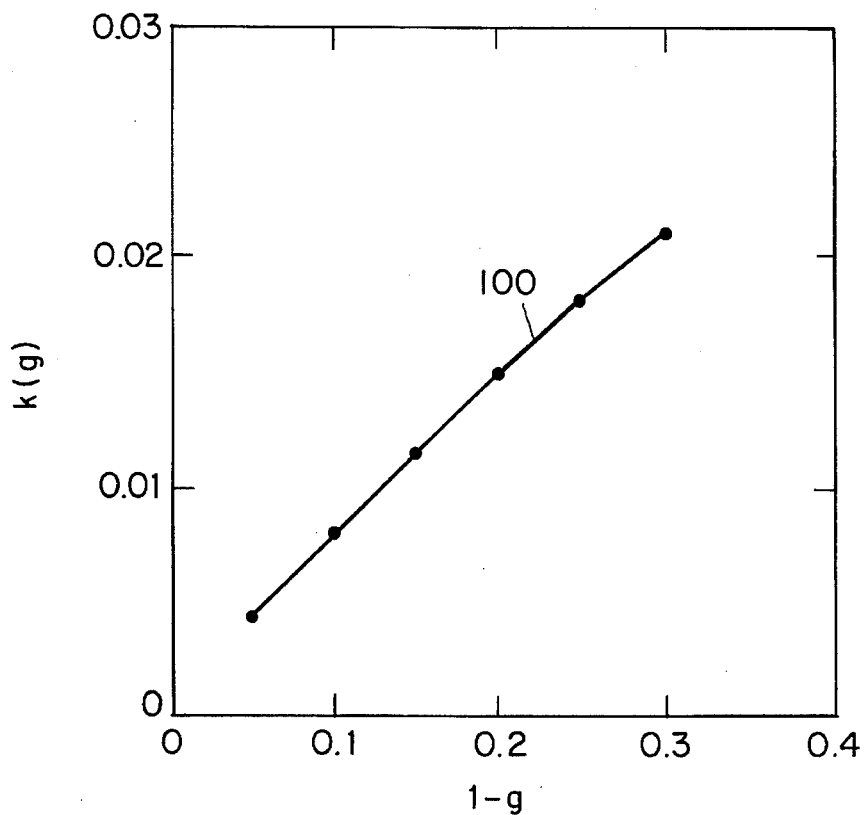
FIG. 5 shows a plot of k(g) determined by fitting eq. (11b) versus 1-g.

In order to test the validity of eq. (13), the diffuse reflectance from a tissue surface was calculated using a Monte Carlo simulation. 10,000 photons were generated in each of the diffuse reflectance calculations. $\mu_s/\mu_a$ was fit to eq. (11b) by varying the single parameter k(g). A plot 100 of k(g) vs. (1-g) is shown in FIG. 5 and demonstrates the good linear correlation predicted by eq. (13), with a slope, S, approximately equal to 1/14. FIG. 4 shows a typical fit 110 of eq. (12) to Monte Carlo simulated data for the reflectance for a variety of $\mu_s$ and $\mu_a$ indicating the utility of this simple formalism for understanding a diverse range of data, $\mu_s/\mu_a$ from 5 to 50.

Note that eq. (11b) and eq. (13) suggest that diffuse reflectance depends on a unique combination of tissue parameters, $-\ln(a)/(1-g)$, and that $R(\mu_a,\mu_s, g)$ can be rewritten in the form:

$$R(\mu_a,\mu_s,g) = \frac{1}{1 - \frac{1}{S}\frac{\ln(a)}{1-g}} \qquad (14)$$

where 1/S=14. This simple equation shows good agreement with the experimentally derived dependence of R on the albedo. In addition, $R(\mu_a,\mu_s,g)$ properly approaches 1 as $\mu_a$ goes to 0. However, the agreement with Monte Carlo simulations begins to break down for values of $\mu_s/\mu_a$ greater than 50. In the following section, a more exact expression for $f_n(g)$ which allows use of this approach over a wide range of tissue parameters, $\mu_s/\mu_a$ from 5 to 300, is derived.

(2) Universal Scattering Probability Distribution

In the previous section we approximated $f_n(g)$ by an exponential function, eq. (10), however, the numerical expression of an exact $f_n(g)$ curve can be obtained from Monte Carlo simulations within the statistical limit of the computation. In this section it is shown that an analytical form of $f_n(g)$ can be approximated from these exact numerical expressions, and that this more precise approach allows the diffuse reflectance to be calculated accurately over a wide range of $\mu_s/\mu_a$, from 5-300, which is typically found for human tissue.

Figure 6:
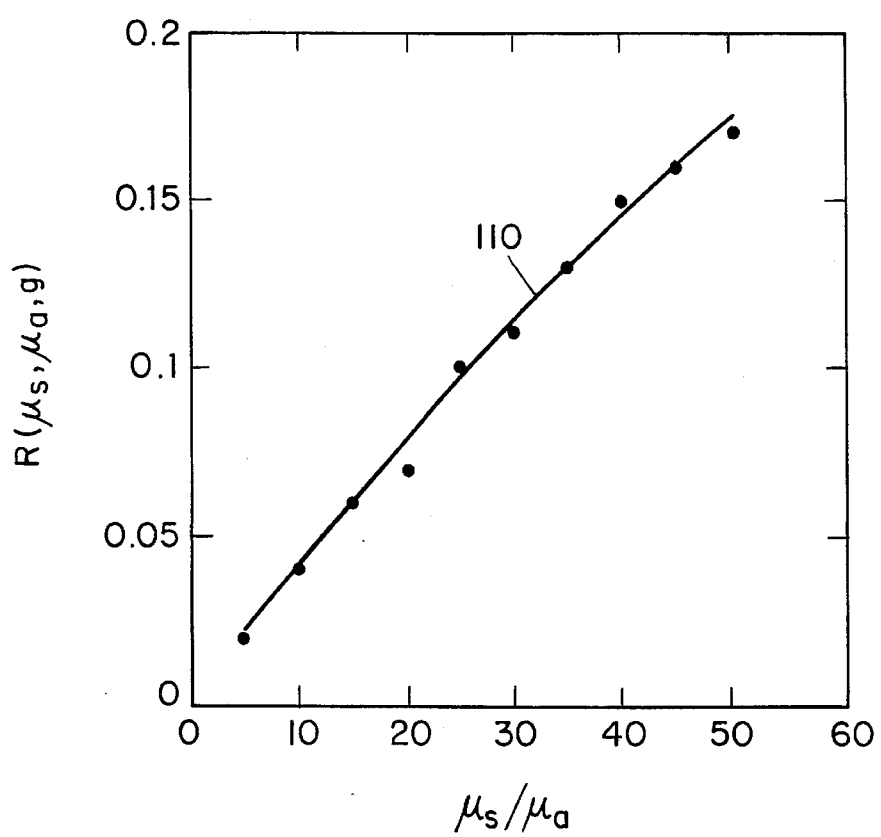
FIG. 6 shows the correlation of reflectance determined from eq. (12) (solid line) to Monte Carlo simulations (solid circles) for g=0.95.
Figure 7:
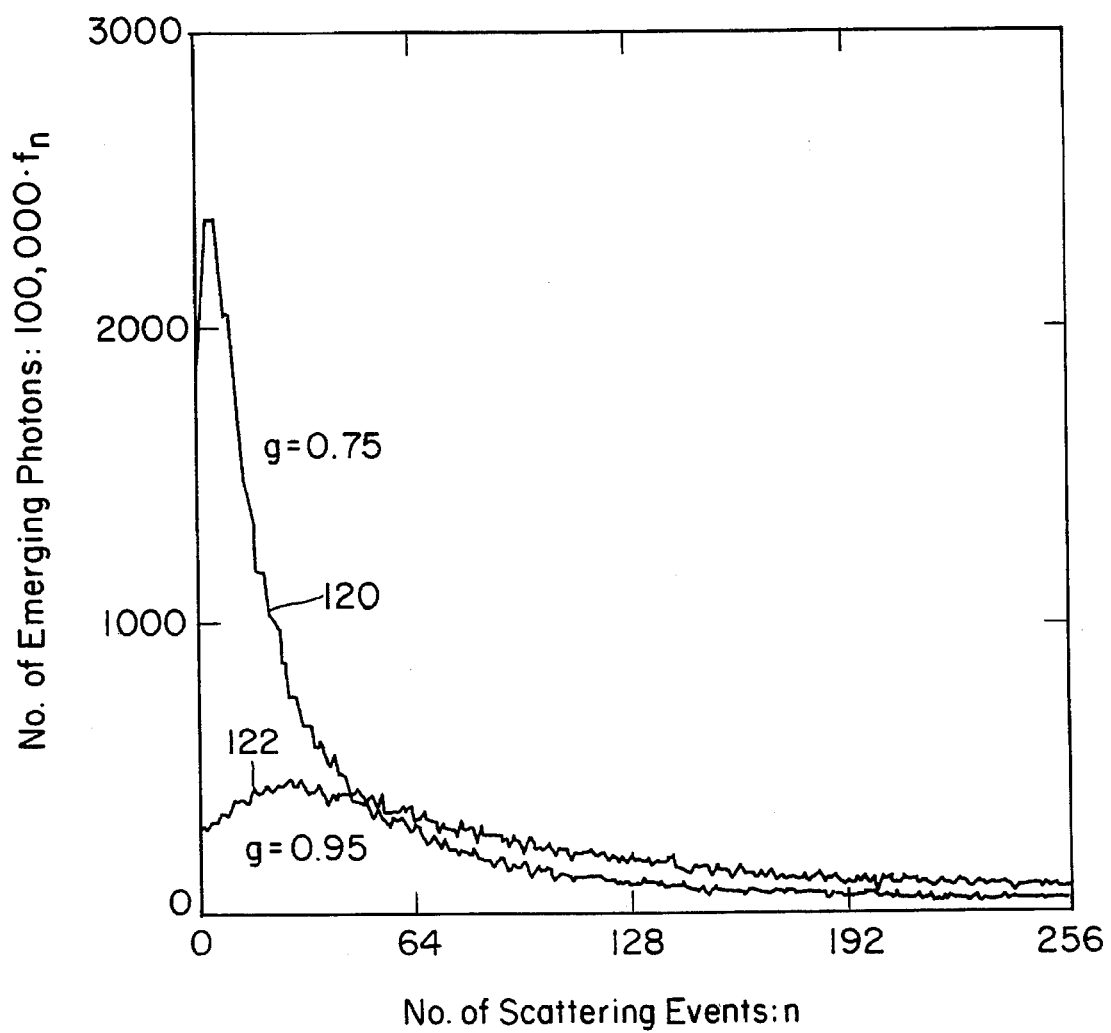
FIG. 7 shows the Monte Carlo simulation for $f_n(g)$, g=0.75 and g=0.95.
Figure 8:
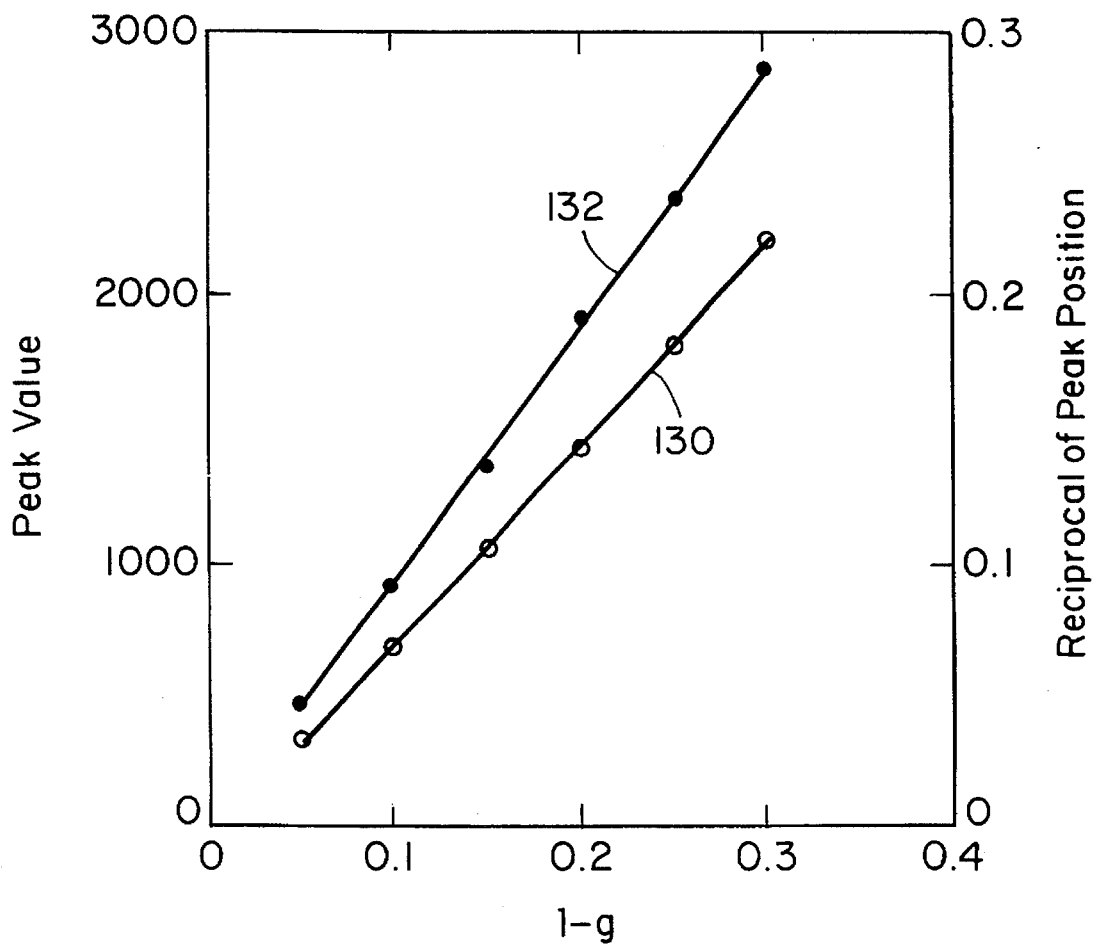
FIG. 8 shows the results of Monte Carlo simulations of fn(g) for several values of g. a) Reciprocal of the peak position of $f_n(g)$ (open circles) versus (1-g); b) Peak value (solid circles) of $f_n(g)$ versus (1-g).

In order to find $f_n(g)$, $f_n(g)$ curves are first calculated via Monte Carlo simulations. An attempt is then made to express the calculated $f_n(g)$ curves by an analytical function. $f_n(g)$ curves were determined for different g values between 0.7 and 0.95 for 100,000 photons. Typical calculated curves 120, 122 are shown in FIG. 7 for several values of g. It can be observed that all the curves show an identical lineshape, rising to peak value for a small number of scattering events, and falling off to zero for a large number of scattering events. In an attempt to determine the functional form of the lineshape as shown in FIG. 8, the reciprocal 130 of the peak position versus (1-g) was found to show a linear relationship. Similarly, as shown in FIG. 6b, the peak intensity was found to have a linear relationship 132 with (1-g). Thus, for all g, if the y axis is scaled by 1/(-g), and the x axis is scaled by (1-g), all the curves can be overlapped, suggesting that $$\frac{f_n(g)}{(1-g)} = W((1-g)n). \tag{15}$$

Equation (15) suggests that for all g, $\mu_s$ and $\mu_a$, there exists a universal probability curve, W, which describes the shape of the escape probability for a photon after n scattering events. Eq. (15) is also consistent with the similarity relations. Note that the scaling method described in eq. (15) does not change the area under $f_n(g)$, which is required by the normalization condition of eq. (8). Once W is determined, the diffuse reflectivity can be calculated.

In order to determine the analytical form of W, the $f_n(g)$ curves were examined individually. $f_n(\mathbf{0.95})$ was chosen for initial analysis while others were used for verification. Random walk movement of a photon on a simple cubic lattice has been described by others. Applying standard arguments in random walk and the central limit theory, it has been shown that for large n $$f_n(0) = \sqrt{\frac{3}{2\pi}}\, n^{-3/2} \tag{16}$$

Applying eq. (15) for g=0.95 implies that $$f_n(0.95) = (0.05)^{-1/2} \sqrt{\frac{3}{2\pi}}\, n^{-3/2} \tag{17}$$

when n is large. Comparison of $f_n(0.95)$ curve determined from Monte Carlo calculations with eq. (17) indicates that this equation is a good approximation in the large n limit; eq. (17) is approximately 5-10% less than the simulations.

The central limit expression, however, cannot be applied in the region of small n. No peak is predicted in the $f_n(g)$ curve, rather, the curve goes as $n^{-1/2}$. Eq. (16) can be re-written to account for the small n limit to yield $$f_n(0) = W(n) = F(n) \sqrt{\frac{3}{2\pi}}\, n^{-3/2} \tag{18}$$

The task then becomes to find F(n). The requirements on F(n) are that F(n) should go to 1 as n is large, and approach zero faster than $n^{+3/2}$ as n approaches 0. Consideration of the curve shape obtained from Monte Carlo simulations suggests that an expression of the form $(1-\exp(-A\,n))^2$ fits these criteria. Thus, eq. (18) can be re-written as $$W(n) = (1 - \exp(-An))^2 \sqrt{\frac{3}{2\pi}}\, n^{-3/2}). \tag{19}$$

In eq. (19), the constant A determines the peak value of the curve. In order to find A, the first derivative of W(n) was obtained and set equal to zero. The result is that A n=0.55. Again, using the g=0.95 curve as our model and eq. (19), A is determined to be 0.45 from the peak value found in the Monte Carlo calculations. Thus, substituting eq. (19) into eq. 915), $f_n(g)$ can be written in final form as $$f_n(g) = (1 - \exp(-0.45(1-g)n))^2 \sqrt{\frac{3}{2\pi(1-g)}}\, n^{-3/2}. \tag{20}$$

Figure 9:
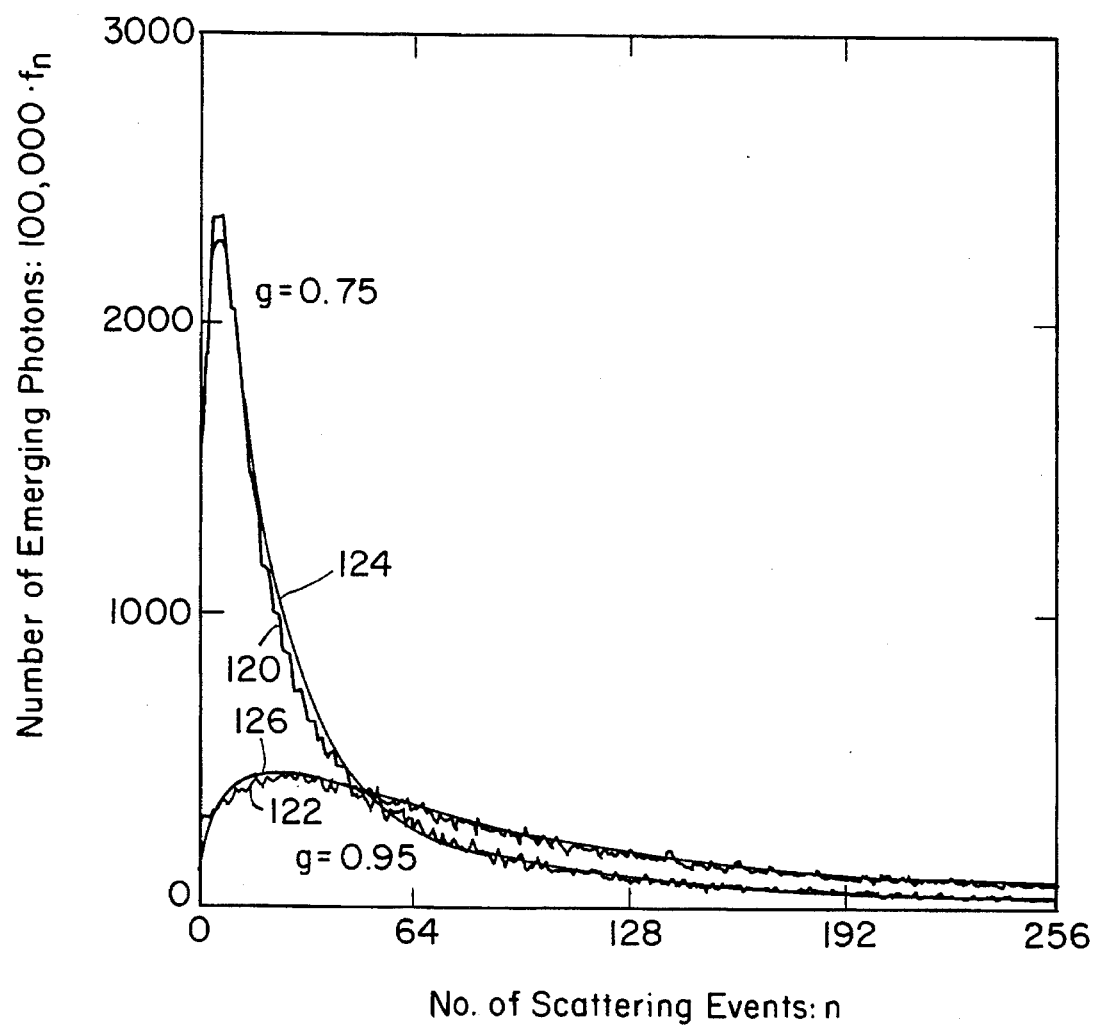
FIG. 9 shows the fit of eq. (20) for $f_n(g)$ to Monte Carlo simulations for g=0.75 and 0.95.

Note that $f_n(g)$ normalizes to 0.97 with the approximation of A from Monte Carlo calculations, which will not affect the diffuse reflectance results. This is because of the small difference between eq. (20) and the simulated data as n approaches infinity. In the reflectance calculation, however, $a^n$ approaches zero as n approaches infinity, compensating for this small difference. FIG. 9 shows that the fit 124, 126 of eq. (20) to the Monte Carlo data for several values of g is excellent.

Equation (20) can now be substituted into eq. (7) to find the diffuse reflectance yielding $$R(\mu_a, \mu_s, g) = \int_0^\infty a^n (1 - \tag{21a}$$

$$\exp(-0.45(1-g)n))^2 \sqrt{\frac{3}{2\pi(1-g)}}\, n^{-3/2}\, dn$$

$$R(\mu_a, \mu_s, g) = \sqrt{6}\left(2\sqrt{0.45 - \frac{\ln(a)}{(1-g)}} - \sqrt{\frac{\ln(a)}{1-g}} - \sqrt{0.9 - \frac{\ln(a)}{(1-g)}}\right) \tag{21b}$$

Figure 10:
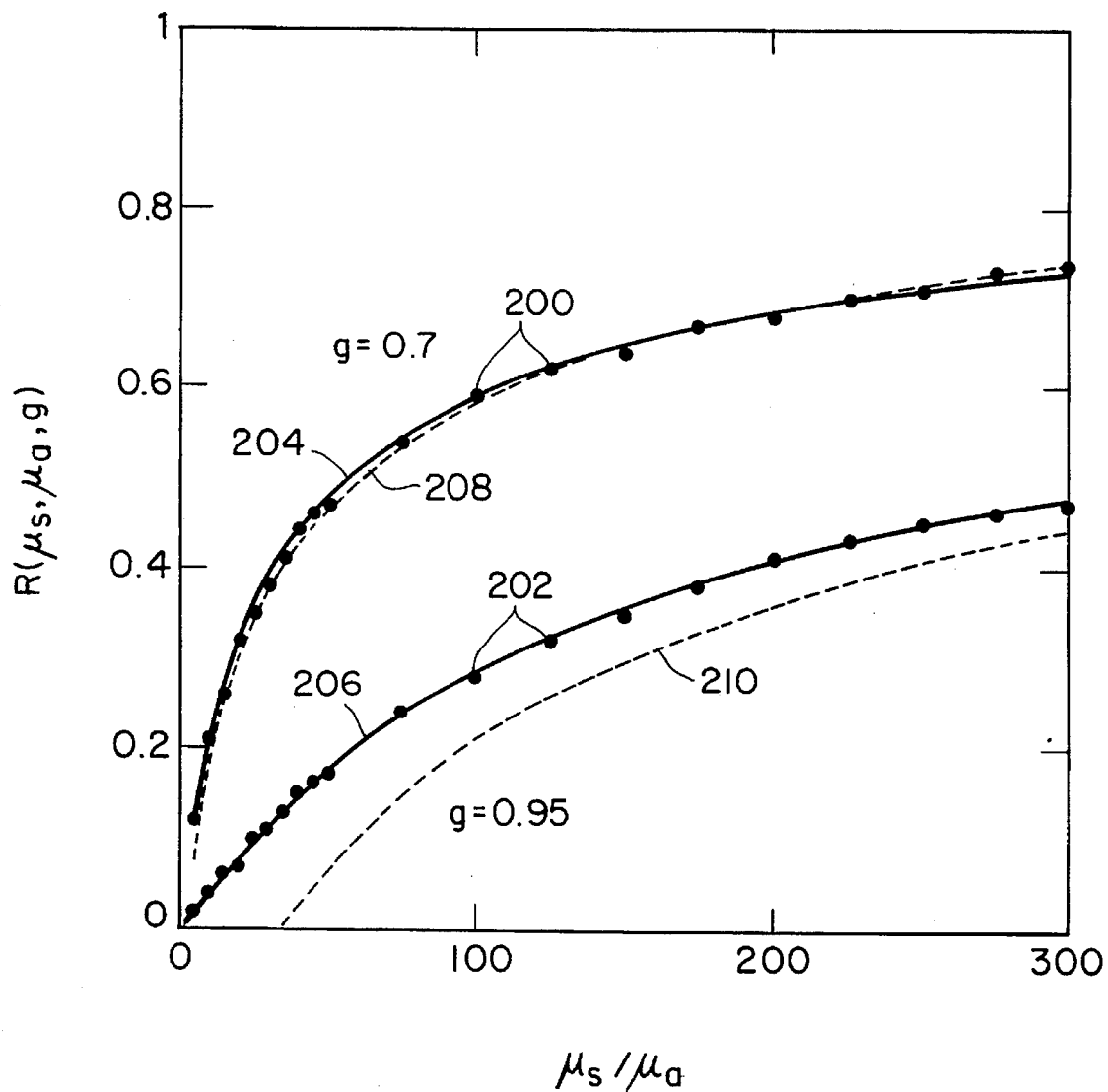
FIG. 10 shows the plot of $R(\mu,\mu,g)$ versus $\mu_s/\mu_a$ for g=0.7 and g=0.95; solid circles, Monte Carlo simulations; solid line, photon migration theory eq. (21b); dotted line, diffusion theory eq. (6).
Figure 11C:
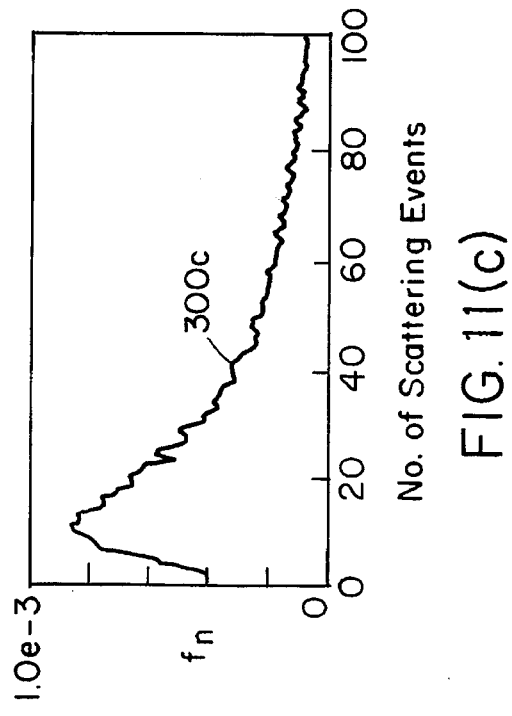
FIGS. 11(a)–11(h) show Monte Carlo simulations of $f_n(g)$ for different collection geometries and boundary conditions. The collection geometries and boundary conditions are summarized in Table 1.
Figure 11D:
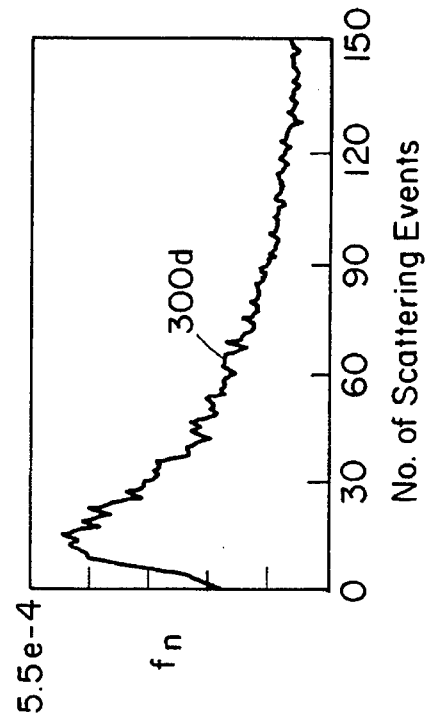
Figure 11A:
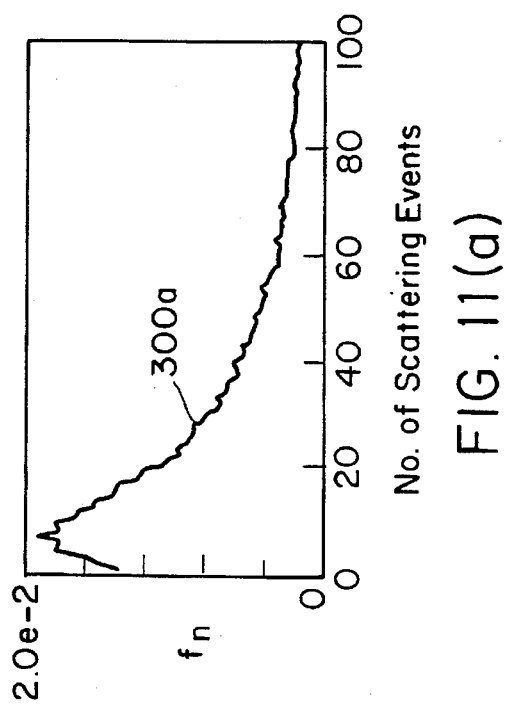
Figure 11B:
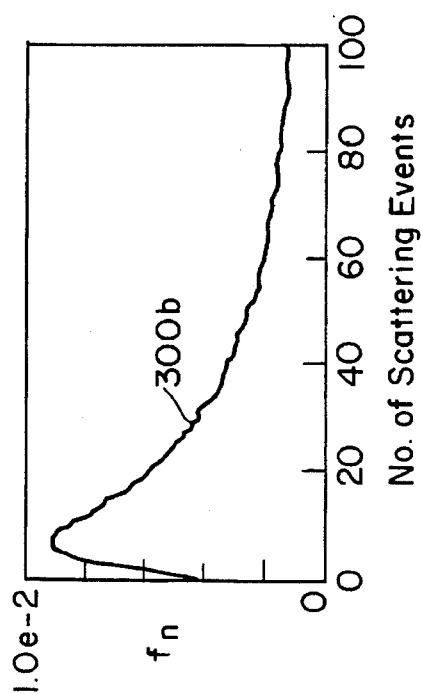
Figure 11E:
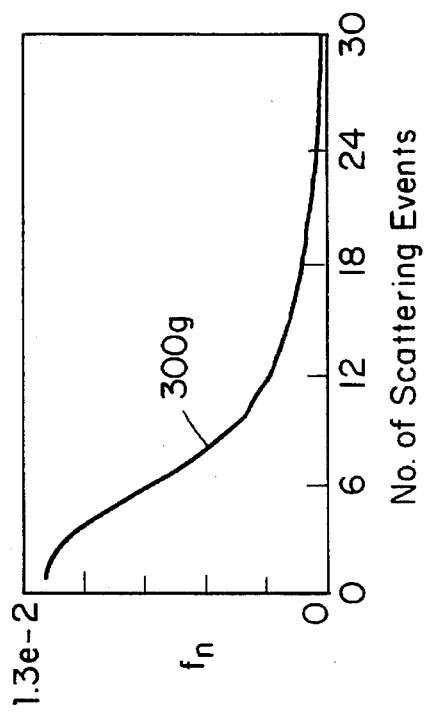
Figure 11F:
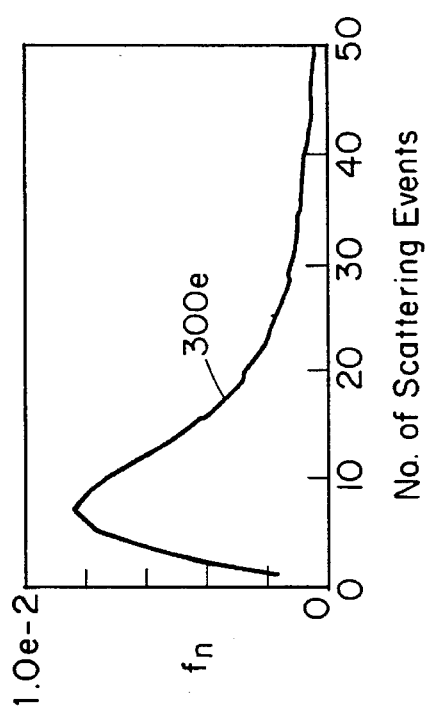
Figure 11G:
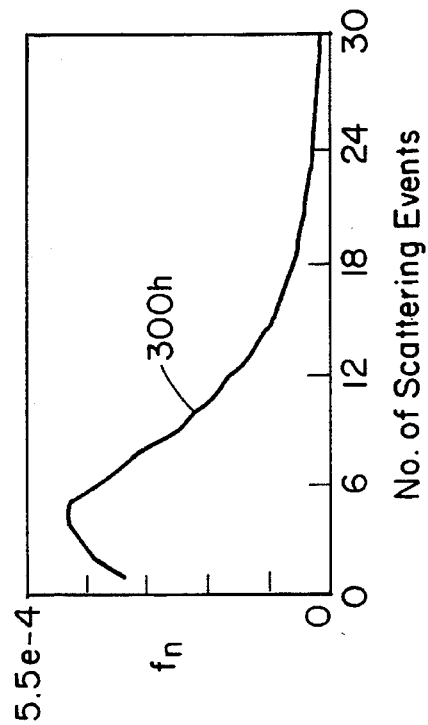
Figure 11H:
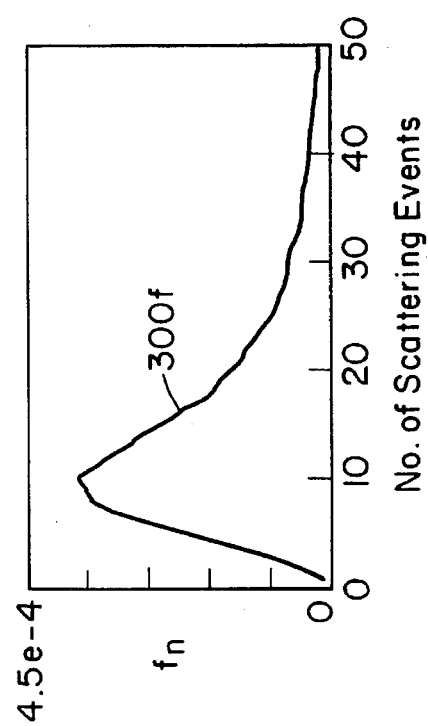

FIG. 10 shows a plot of $R(\mu_a,\mu_s,g)$ versus $\mu_s/\mu_a$ for g=0.7 and g=0.95 respectively as calculated from Monte Carlo simulations 200, 202, the photon migration approach 204, 206, eq. (21b) and diffusion theory 208, 210, eq (6), for wide range of $\mu_s/\mu_a$, 5 to 300. In the case of g=0.7, the diffusion approximation is valid and the fit of both eq. (21b) and diffusion theory are equally valid. However, for g=0.95, diffusion theory is particularly poor while eq. (21b) still fits the data well. Note again the unique dependence of $R(\mu_a, \mu_s,g)$ on -ln(a)/(1-g) and that $R(\mu_a,\mu_s,g)$ goes to 0.97 as $\mu_a$ goes to 0.

For the full range of optical parameters typically found in human tissue, $\mu_s/\mu_a$ from 5 to 300, and g from 0.7 to 0.95, eq (21b) is accurate with an error of less than 1% when compared to Monte Carlo reflectance calculations. Since $R(\mu_a,\mu_s,g)$ approaches 0.97 as approaches infinity, the maximum error in eq. (21b) should always be smaller that 3% for any value of and $\mu_a$.

In eq. (21b), the dependence of diffuse reflectance, R, on the tissue optical parameters, $\mu_a$, $\mu_s$ and g, is demonstrated using the photon migration formalism. Thus, the diffuse reflectance can be measured experimentally to determine the tissue optical parameters if $$\frac{-\ln(a)}{(1-g)}$$

can be written in terms of R. Renaming the quantity $$\frac{-\ln(a)}{(1-g)}$$

as J, eq. (21b) can be transformed to a cubic equation of J of the form:

$$J^3 + \alpha J^2 + \beta J + \gamma = 0 \qquad (22)$$

where $\alpha$, $\beta$ and $\gamma$ are real functions of the measurable quantity R and given by:

$$\alpha = 3A - \frac{9}{16} R'^2 \qquad (23)$$

$$\beta = 2A^2 + \frac{3}{32} (4A^2 - 12R'^2 A + R'^4)$$

$$\gamma = \frac{(4A^2 - 12R'^2 + R'^4)^2}{256 R'^2}$$

and $A=0.45$, $R^1=R/+b$ 6. Taking $J'=J+\alpha/3$, eq. (22) can be further transformed:

$$J'^3 + 3\alpha^1 J^1 + 2\beta' = 0 \qquad (24)$$

where $$\alpha' = \frac{1}{3} \left[ \beta - \frac{\alpha^2}{3} \right] \qquad (25)$$

$$\beta' = \frac{1}{2} \left( \gamma - \frac{\alpha\beta}{3} + \frac{2\alpha^3}{27} \right)$$

The real root of eq. (24) is given by $$J' = \sqrt[3]{\beta' + \sqrt{\beta'^2 + \alpha'^3}} - \sqrt[3]{\beta' - \sqrt{\beta'^2 + \alpha'^3}} \qquad (26)$$

With eq. (26), $$J(a, g) = \frac{-\ln(a)}{(1-g)}$$

can be analytically calculated from the diffuse reflectance spectrum. Since g is approximately independent of irradiation wavelength for a given type of tissue, the albedo is obtained as a function of incident wavelength. Thus, the physical parameters of tissue may be probed as a function of disease by measuring the diffuse reflectance. It is interesting that the diffuse reflectance is a function of the single fundamental parameter, $$J(a,g) = \frac{-\ln(a)}{(1-g)},$$

both in the simple formalism presented in eq. (14) and eq. (21b). The general nature of this parameter in other boundary conditions is scrutinized using this formalism.

Although other methods based on approximations of the transport equation for the diffuse reflectance, such as the delta-Eddington approximation, yield comparable accuracy to the method presented here, the photon migration method would be preferred over these techniques for the following reasons. First, the invertability of eq. (21b) provides a convenient method for extracting the basic optical parameters from the diffuse reflectance with having to resort to curve fitting. This makes the photon migration technique more amenable to use in real-time systems. Secondly, the simplicity and accuracy of this approach is based on the successful separation of the phase dependence of the scattering from the other tissue parameters, $\mu_a$ and $\mu_s$. This parameter separation allows more complex and realistic geometries, such as optical fiber techniques and index-mismatched boundary conditions, to be modeled with simple, accurate analytical equations as will be demonstrated in future work. In other approaches, analytical expressions are either exceedingly complex or not available for these types of geometries. Finally, this method has allowed the discovery of the fundamental quantity, $$J(a,g) = \frac{-\ln(a)}{(1-g)},$$

which acts as the basic scaling factor to completely determine the diffuse reflectance.

It is possible to extend this approach to optical-fiber geometries, index-mismatch boundary conditions, and fluorescence and Raman scattering spectroscopy of tissue. The mathematical convenience, high accuracy, and analytical form of the results make this approach extremely promising for use is real time clinical applications.

FLUORESCENCE ANALYSIS

Diffusion Theory Calculation for Fluorescence

From diffusion theory an expression can be determined for the observed bulk tissue fluorescence intensity, $F(\lambda_x, \lambda_m)$, from a semi-infinite slab:

$$F(\lambda_x, \lambda_m) = \mu_a(\lambda_x) \phi(\lambda_x, \lambda_m) \left[ \frac{4\pi A(\lambda_x) + F_o}{\mu_t(\lambda_x) + \kappa_d(\lambda_m)} + \frac{4\pi C_2(\lambda_x)}{\kappa_d(\lambda_x) + \kappa_d(\lambda_m)} \right] C(\lambda_m) \qquad (27)$$

where $\lambda_x$ and $\lambda_m$ are the excitation and emission wavelengths, respectively. The other quantities are fully described in the section below entitled "One-Dimensional Diffusion Calculation for Fluorescence". Although eq. (27) could be used to fit an experimentally obtained spectrum, it does not provide a practical method for extracting the quantum yield or intrinsic fluorescence, $\phi(\lambda_x, \lambda_m)$, from the optically thick tissue spectrum. As will be seen below, the photon migration picture provides such an expression directly.

Monte Carlo Methods

The Monte Carlo method discussed above with respect to the diffuse reflectance analysis is now applied to the fluorescence analysis in an analogous manner. In this approach, a photon injected into tissue is allowed to travel freely for approximately one mean free path before it interacts with a tissue particle. Upon interaction, the photon is either scattered, absorbed, or re-emitted as fluorescence. If scattered or re-emitted as fluorescence, it travels in a new direction determined by the phase function for scattering or fluorescence. For a semi-infinite slab of tissue, the process is allowed to continue until either the photon is absorbed or re-emitted out of the tissue.

In order to simulate this process, the Monte Carlo method uses a random number generator to sample random variables, such as the path length between two interaction events, the occurrence of absorption, fluorescence, and the scattering angle. The values of these variables are chosen randomly from their probability distributions. In these fluorescence simulations, the following probability distribution functions and rules are utilized:

1. The probability of a photon traveling a path length, L, is determined by the sum of the absorption and scattering coefficients, $\mu_t=\mu_s+\mu_a$. Using Beer's law, the probability distribution function of the path length, p(L), is given by $p(L)=\mu_t \exp(-\mu_t L)$.

2. The probability of a photon being absorbed upon interaction with a tissue particle, p(A), depends on both the absorption and the scattering coefficients, and is given by $$P(A) = \frac{\mu_a}{\mu_s + \mu_a}.$$

3. Upon absorption, the probability of generating a fluorescence photon from an excitation wavelength, $\lambda_m$, is given by the quantum yield, $\phi(\lambda_x, \lambda_m)$. This represents the intrinsic tissue fluorescence, unaffected by scattering, absorption, geometry, or boundary conditions.

4. Fluorescence is emitted isotropically (i.e. the anisotropy coefficient g=0).

5. The deflection angle in a single scattering event is determined by the Henyey-Greenstein phase function, which is known to provide a particularly good representation of the scattering in tissue.

6. The internal reflection versus transmission at the boundary is determined by Fresnel's reflection relationships and Snell's law.

Using a large number of photons, the Monte Carlo method allows a statistically precise result to be obtained. Therefore, it usually serves as a reliable standard to test the accuracy of other models. The Monte Carlo programs utilized in this analysis showed agreement with standard results.

In the photon migration method the phase dependence of the scattering is separated from the scattering and absorption coefficients by introducing an escape probability distribution function, $f_n(g)$, which describes the probability of a photon with scattering anisotropy coefficient, g, escaping from a semi-infinite slab of tissue after n scattering events. For a semi-infinite slab of tissue which is optically thick, every photon is eventually re-emitted out of the tissue, but with a reduced weight reflecting the number of interactions the photon has undergone before leaving the tissue. For a photon scattered n times before being re-emitted from the tissue, the weight of the photon is given by $a^n$, where $a=\mu_s/(\mu_a+\mu_s)$, the albedo. The diffuse reflectance, R, is then given by eg. (7).

Using this approach, two analytical expressions were derived that could be used to calculate R, as a function of the quantity $-\ln(a)/(1-g)$. Under the simplifying assumption that the $f_n(g)$ curve can be represented an exponential decreasing function of n, given by eg. (14), where S is a constant approximately equal to $^{+b}$ 1/14. Equation (14) agrees with both the Monte Carlo calculations and experimental data within a range $\mu_s(1-g)/\mu_a<10$, which covers many human tissues currently being examined. A more general expression for R was also derived earlier (eqs. (11a) and (11b)), but only eq. (14) will be utilized in the derivation be low for the fluorescence signal.

Monte Carlo Simulations of the $f_n(g)$ Curves

Equation (14) is derived in the semi-infinite geometry and under index-matched boundary conditions by approximating the $f_n(g)$ curve by an exponential function. Eq. (14) can be extended if it can be demonstrated that $f_n(g)$ behaves similarly under a diverse set of collection geometries and boundary conditions. FIGS. 11(a)–11(h) show the calculated form of $f_n(g)$ from Monte Carlo simulations for several different boundary conditions and geometries. A value of g=0.8, typical of biological tissue, was assumed. The geometry and boundary condition for each $f_n(g=0.8)$ curve studied is summarized in Table 1.

TABLE 1

Summary of the geometries and boundary conditions for calculating the $f_n$ (g = 0.8) curves shown in FIGs. 11(a)–11(h)

| FIG. No. | Light Delivery | Collection Area | Collection Angle | Relative Refractive Index |
|---|---|---|---|---|
| 11.(a) | plane wave | infinitely wide[1] | 0°–90° | 1.0 |
| 11.(b) | plane wave | infinitely wide[1] | 0°–90° | 1.4 |
| 11.(c) | plane wave | infinitely wide[1] | 0°–12.7° | 1.0 |
| 11.(d) | plane wave | infinitely wide[1] | 0°–12.7° | 1.4 |
| 11.(e) | optical fiber[2] | D/2 < r < D | 0°–90° | 1.0 |
| 11.(f) | optical fiber[2] | D/2 < r < D | 0°–12.7° | 1.0 |
| 11.(g) | optical fiber[2] | 0 < r < D/2 | 0°–90° | 1.0 |
| 11.(h) | optical fiber[2] | 0 < r < D/2 | 0°–12.7° | 1.0 |

[1]The same result is expected independent of the light delivery profile when the light collection area is infinitely wide.
[2]Uniform and collimated beam is assumed out of the optical fiber end with a diameter D = 6/$\mu_t$; this represents a typical in vivo experimental geometry utilizing a 200 μm core fiber with a tissue attenuation coefficient of $\mu_t$ = 30 mm$^{-1}$.

All of the $f_n(g)$ curves 300a–300h of FIGS. 11(a)–11(h), respectively, exhibit a similar lineshape, rising to a peak value for a small number of scattering events, and falling to zero for a large number of scattering events. However, the x and y scales in each of the curves in FIG. 11 are different. The index-mismatched boundary conditions (FIG. 11(a) versus 11(b), 11(c) versus 11(d)) tend to spread the $f_n$ curve in the x direction and compress it in the y direction. On the other hand, the fiber probe geometry (FIG. 11(a)–(d) versus 11(e)–(h)) tends to compress the $f_n$ curve in both the x and y scales. This suggests that an exponential function can still be used to approximate $f_n(g)$, except that the numerical constants in the exponential function will depend on the geometry. The effect on eq. (14) is that:

$$R = \frac{\kappa_o}{1 - \frac{1}{S'} \frac{\ln(a)}{1-g}} \quad (28)$$

where $k_o$ is the normalization constant (replacing 1). Both $k_o$ and S' are constants for a given geometry and refractive index mismatch at the boundary.

Fluorescence Photon Migration

In the photon migration picture, upon interaction with a tissue particle, an incident photon is always scattered with its weight reduced by a factor $a(\lambda_x)$, depositing $(1-a(\lambda_x))$ of its weight in the tissue. Upon absorption, the photon has a certain probability of being re-emitted at a fluorescence wavelength $\lambda_m$ which is given by the quantum yield $\phi(\lambda_x, \lambda_m)$. The weight of the fluorescent photon is then $(1-a(\lambda_x))\phi(\lambda_x,\lambda_m)$ times the original weight of the incident photon just before the interaction. The fluorescent photon is emitted isotopically and undergoes scattering on its way out of the tissue, lowering its weight by $a(\lambda_m)$ at each scattering interaction. In this model, it is assumed that the secondary fluorescence generated by the fluorescence photons is negligible. Therefore, only incident photons which are at wavelength $\lambda_x$ are permitted to generate fluorescent photons at wavelength $\lambda_m$.

Figure 12:
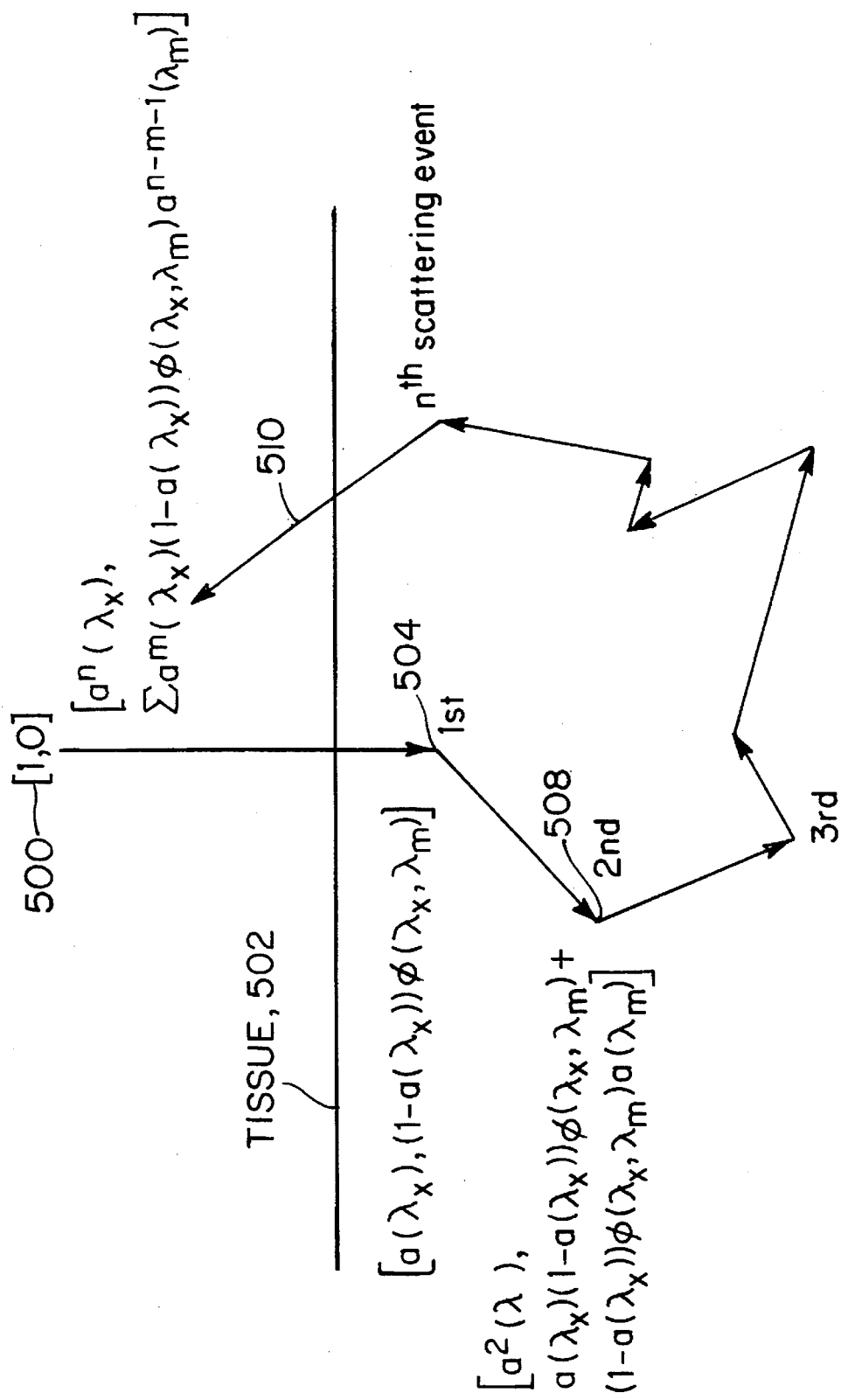
FIG. 12 shows a photon migration picture of fluorescence.

Initially, two temporary restrictions are imposed, which are removed later: (1) The fluorescence "anisotropy" coefficient is equal to the tissue scattering anisotropy coefficient, g, which is considered to be the same for both the excitation and emission photons; and (2) the total extinction coefficient, $\mu_t$, at the excitation and emission wavelengths are assumed equal. Since the photon path is determined by g and $\mu_t$, the incident excitation photon and the fluorescent photon induced by it will follow the exactly same path under the above conditions. FIG. 12 shows an example of a photon path in which an incident photon 500, entering tissue 502 with an initial weight of one, is scattered n times along its path, and thus induces n fluorescent photons. Utilizing the notation $[w(\lambda_x), w(\lambda_m)]$ to represent the photon weights at the excitation and emission wavelength, respectively, after the first scattering event 504 a fluorescence photon is generated, and the photon weights are given by $[a(\lambda_x), (1-a(\lambda_x))\phi(\lambda_x, \lambda_m)]$. After the second scattering event 508, the weight of the incident photon is reduced again by the factor $a(\lambda_x)$, and the weight of the first fluorescent photon is reduced by the factor $a(\lambda_m)$. In the meantime, a second fluorescence photon with weight of $a(\lambda_x)(1-a(\lambda_x))\phi(\lambda_x,\lambda_m)$ is induced by the incident photon. Now, in accordance with this notation, the photon weights are written as $[a^2(\lambda_x), (1-a(\lambda_x))\phi(\lambda_x,\lambda_m)a(\mu_m)+a(\lambda_x)(1-a(\lambda_x))\phi(\lambda_x,\lambda_m)]$. When the photon emerges 510 after n scattering events, the weights become $$\left[ a^n(\lambda_x), \sum_{m=0}^{n-1} a^m(\lambda_x)(1-a(\lambda_x))\phi(\lambda_x, \lambda_m)a^{n-m-1}(\lambda_m) \right].$$

Summing the total fluorescence weight over all the possible paths yields:

$$F(\lambda_x, \lambda_m) = \sum_{n=1}^{+\infty} f_n(g) \qquad (29)$$

$$\left( \sum_{m=0}^{n-1} a^m(\lambda_x)(1-a(\lambda_x))\phi()\lambda_x, \lambda_m \right) a^{n-m-1}(\lambda_m) \right) =$$

$$(1-a(\lambda_x))\phi(\lambda_x, \lambda_m) \frac{R(a(\lambda_x), g) - R(a(\lambda_m), g)}{a(\lambda_x) - a(\lambda_m)}$$

making use of the relationship $$R(a, g) = \sum_{n=1}^{\infty} a^n f_n(g).$$

Note that eq. (29) is derived without any assumption about the experimental geometry or the tissue boundary conditions. This suggests that this equation can be utilized to extract the systemindependent quantum yield, $\phi(\lambda_x, \lambda_m)$, for any experimental geometry as long as we measure the optically thick bulk fluorescence, F, and the diffuse reflectance, R, are measured in the same manner. The method propounded by eq. (29) suggests that the intrinsic fluorescence extracted from measurement of the diffuse reflectance and bulk fluorescence balances out any effects of geometry or boundary conditions.

In order to apply the model to realistic situations, the two restrictions invoked in deriving eq. (29) are removed. In this model, g is assumed to be constant at all wavelengths of the fluorescence spectrum. This is based on the fact that the changes in g over wavelengths of interest are generally small, and do not significantly change the fluorescence spectrum. However, in the fluorescence event, the photon is always emitted isotropically. A quantity called the effective anisotropy coefficient, $g_{eff}$, is introduced which is defined as the average value of (N-1) forward directed scattering events with anisotropic coefficient g, and a single isotropic fluorescence event with $g_{fluorescence}=0$. This is written as:

$$g_{eff} = \frac{(N-1)g}{N} \qquad (30)$$

where N is the peak position of the $f_n(g)$ curve. In the case of a semi-infinite slab of tissue, Monte Carlo simulations indicate that $N(1-g)=1.3$ for index-matched boundary conditions, and 2.0 for index-mismatched boundary conditions (with relative indices of refraction of 1.4).

Secondly, it was initially assumed that $\mu_t$, which determines the mean step length of photon migration, is the same at the excitation and emission wavelengths. This is not necessarily true. Thus, the number of scattering events required for the photon to emerge from the tissue will also change. If it is assumed that the fluorescence photon follows the path described by the model, another quantity, an effective albedo, $a_{eff}(\lambda_m)$, can be introduced in order to correctly estimate the final weight of the emerging fluorescence photon. In order to do so, a general result of random walk theory is considered, which states that the distance, D, traveled by a random walker after m steps relates to its step length, via the equation $D^2=ml^2$. Thus, in the index-matched case, the effective albedo can be scaled from the true albedo using the relation:

$$a_{eff} = a^{\frac{\mu_t^2(\lambda_m)}{\mu_t^2(\lambda_x)}} \qquad (31)$$

Under the index-mismatched boundary conditions, it is necessary to differentiate two types of fluorescence photons, those which are not internally reflected at the tissue surface, and those which are internally reflected and continue their travel within tissue afterwards. The effective albedo for the first type is the same as in the index-matched case; however, the effective albedo for the second type is assumed unchanged from the actual albedo, $a(\lambda_m)$, because, according to the physical picture presented above in the diffuse reflectance case, the weight change along a path between two points, both at the surface, does not depend on the mean step length when the tissue is considered optically thick. Thus, more generally, the effective albedo is approximated by:

$$a_{eff} + r_d a + (1-r_d) a^{\frac{\mu_t^2(\lambda_m)}{\mu_t^2(\lambda_x)}} \qquad (31')$$

where $r_d$ is the probability of a photon being internally reflected at the boundary. In this case, ra is equal to 0 for the index-matched boundary conditions, and 0.53 for the index-mismatched boundary conditions (with relative indices of refraction of 1.4).

By replacing g and $a(\lambda_m)$ with $g_{eff}$ and $a_{eff}(\lambda_m)$, respectively, and noting that $a_{eff}(\lambda_x)$ is just $a(\lambda_x)$, eq. (29) becomes:

$$F(\lambda_x,\lambda_m) = (1 - a(\lambda_x))\phi(\lambda_x,\lambda_m) \frac{R(a(\lambda_x),g_{eff}) - R(a_{eff}(\lambda_m),g_{eff})}{a(\lambda_x) - a_{eff}(\lambda_m)} \quad (32)$$

Equation (32) can be simplified by expressing the albedo, a, as a function of R. For the semi-infinite geometry and index-matched boundary conditions, eq. (14) is used, with $-\ln(a)$ expanded as $(1-a)$ when $\mu_s \gg \mu_a$. Then, eq. (32) becomes:

$$F(\lambda_x,\lambda_m) = \phi(\lambda_x,\lambda_m)(1 - R(a(\lambda_x),g_{eff}))R(a_{eff}(\lambda_m), g_{eff}) \quad (33)$$

which for single wavelength excitation can be written as:

$$\phi(\lambda_m) = q \frac{F(\lambda_m)}{R(a_{eff}(\lambda_m),g_{eff})} \quad (34)$$

where q is a proportionality constant which depends on the excitation wavelength. In eq. (34), the optically thick bulk fluorescence spectrum, $F(\lambda_m)$, is measured in the experiment, whereas the "effective" reflectance, $R_{eff} = R(a_{eff}(\lambda_m), g_{eff})$, cannot be directly measured. However, $R_{eff}$ can be related to the measured diffuse reflectance R, using eqs. (14). and (31):

$$\frac{\frac{1}{R_{eff}} - 1}{\frac{1}{R} - 1} =$$

$$\frac{1-g}{1-g_{eff}} \left( r_d + (1 - r_d) \frac{\mu_t^2(\lambda_m)}{\mu_t^2(\lambda_x)} \right) \approx$$

$$\frac{1-g}{1-g_{eff}} \left( r_d + (1 - r_d) \frac{\mu_s^2(\lambda_m)}{\mu_s^2(\lambda_x)} \right) \quad (35)$$

Since both g and $\mu$, vary little in different samples of the same tissue, (M. Keijzer, R. R. Richards-Korum, S. L. Jacques and M. S. Feld, "Fluorescence spectroscopy Of turbid media: autofluorescence of human aorta", Appl. Opt. 14, 4286–4292 (1989)) eq. (35) suggests that the shape of $\phi(\lambda_m)$ in eq. (34) can be easily extracted by measuring F and R.

Note that in deriving eq. (33), eq. (14), which is appropriate for a semi-infinite geometry and indexmatched boundary condition, was utilized. If this approach is applied to other geometries and boundary conditions, eq. (33) must be modified using eq. (28'). However, eq. (34) will remain the same except that the numerical proportionality constant, q, will be different, depending through $k_0$ on the specific geometry and boundary conditions. Thus, as long as the optically thick bulk tissue fluorescence, F, and the diffuse reflectance, R, are measured at the same time, the intrinsic lineshape information in $\phi(\lambda_m)$ can be extracted using eq. (34). This is true in this technique because the fluorescence and the reflectance photons effectively follow the same path, so that all the system-dependence of the fluorescence is retained in the diffuse reflectance measurement. The extracted $\phi(\lambda_m)$ is therefore a system independent quantity, equivalent to measuring the fluorescence from a thin tissue specimen which is unaffected by absorption and scattering. Furthermore, in certain practical situations where the geometry and boundary conditions can be made reproducible, the constant q can be calibrated, and the measurement will then yield calibrated intensity information as well.

EXPERIMENTAL RESULTS

Monte Carlo Simulations for a Semi-infinite Slab

Both Monte Carlo simulations and tissue experiments have been carried out in order to verify the theory presented above. In the Monte Carlo calculations, the tissue optical parameters, $\mu_a$, $\mu_s$, g and 4, of human aorta intima and media, summarized in Table 2, were utilized to simulate the fluorescence.

TABLE 2

Summary of the arotic tissue optical parameters from the literature, utilized in the Monte Carlo simulations.

| $\lambda$(mm) | 476[1] | 500 | 520 | 540 | 560 | 580 | 600 | 620 | 640 |
|---|---|---|---|---|---|---|---|---|---|
| | | | | Intima: | | | | | |
| $\phi$(a.u.) | | 66 | 100 | 95 | 83 | 61 | 49 | 34 | 24 |
| $\mu_a$ (mm$^{-1}$) | 1.3 | 1.0 | 0.8 | 1.0 | 0.8 | 1.0 | 0.4 | 0.4 | 0.4 |
| $\mu_s$ (mm$^{-1}$) | 29.0 | 27.5 | 24.8 | 24.7 | 23.3 | 21.8 | 20.4 | 20.0 | 19.6 |
| g | 0.84 | 0.84 | 0.84 | 0.84 | 0.84 | 0.84 | 0.84 | 0.84 | 0.84 |
| | | | | Media: | | | | | |
| $\phi$(a.u.) | | 66 | 100 | 95 | 83 | 61 | 49 | 34 | 24 |
| $\mu_a$ (mm$^{-1}$) | 0.70 | 0.55 | 0.50 | 0.60 | 0.45 | 0.50 | 0.25 | 0.25 | 0.25 |
| $\mu_s$ (mm$^{-1}$) | 48.0 | 45.5 | 43.5 | 40.5 | 38.5 | 37.0 | 36.0 | 35.0 | 33.5 |
| g | 0.9 | 0.9 | 0.9 | 0.9 | 0.9 | 0.9 | 0.9 | 0.9 | 0.9 |

[1]Excitation wavelength.

The results were compared to the technique presented herein, eq. (32), as well as to both the Eddington approximation and the delta-Eddington approximation to diffusion theory discussed above. In each simulation, 10,000 incident photons in a 1 mm plane wave impinged perpendicularly on a 10 mm thick slab of tissue, and the number of all the fluorescence photons emerging from the upper surface was recorded. No photons were observed to emerge from the back surface.

Figure 13A:
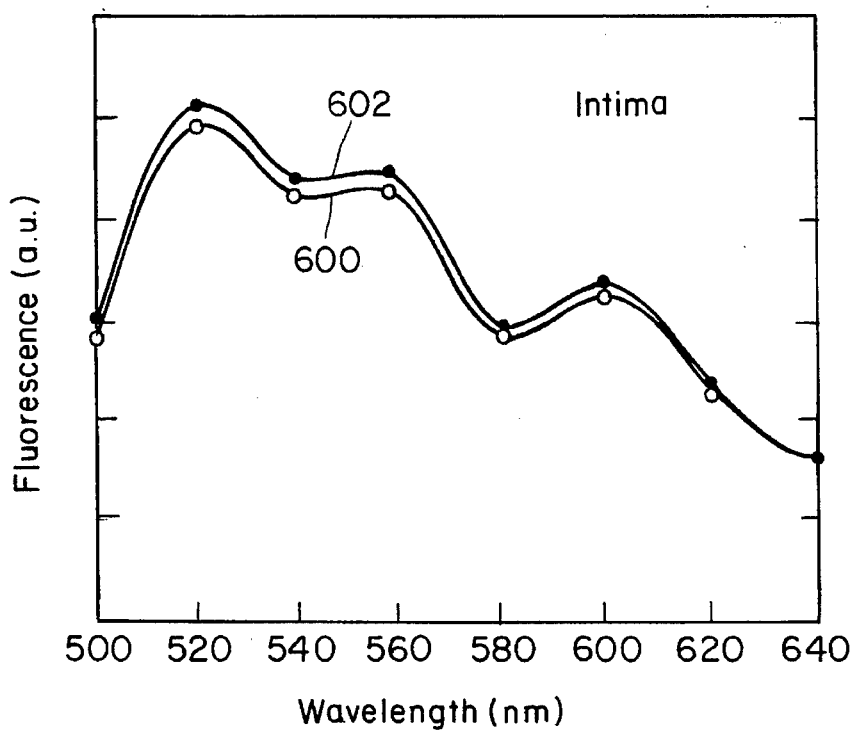
FIGS. 13(a) and 13(b) show a comparison of photon migration model with Monte Carlo for (a) intima and (b) media. The open circles are data points from eq. (32) and the solid circles are Monte Carlo simulations. The lines are cubic spline curve fits to the data points
Figure 13B:
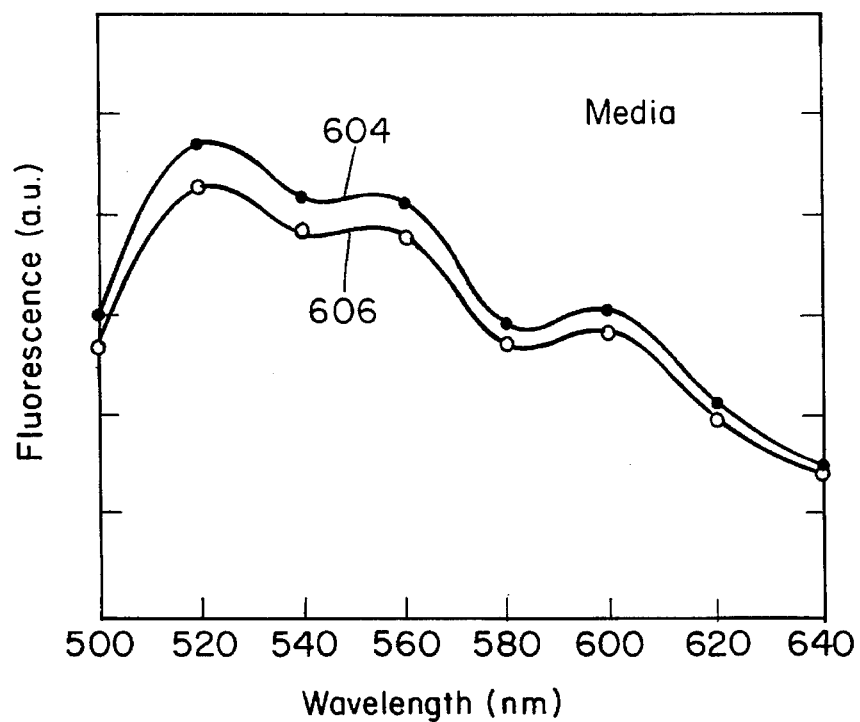

FIG. 13(a) and 13(b) compare the results of Monte Carlo simulations with eq. (32) for two cases with tissue parameters taken from arterial intima and media with a semi-infinite geometry and an index-matched boundary condition assumed. When utilizing the known tissue parameters from intima (FIG. 13(a)), the difference between the model 600 and Monte Carlo simulation 602 is less than 5% over the entire spectrum. In this case the anisotropy coefficient is 0.84. When g is raised to 0.9, as is measured for aortic media, the difference between the Monte Carlo simulation 604 and eq. (32) 606 is on the order of 10% (FIG. 13b). The reason for the discrepancy at higher values of g can be understood from the evaluation of $g_{eff}$ in eq. (30). Since the value of scattering events at which the escape probability curve is a maximum, N, approaches infinity as g approaches 1, $g_{eff}$ approaches g at higher g values. In the limit that g approaches 1, the diffuse reflectance goes to 0; thus the model of eq. (32) predicts zero fluorescence intensity, which is clearly incorrect. On the other hand, $g_{eff}$ is exactly the same as g when photons are scattered isotropically. Thus, the approximation for $g_{eff}$ is more appropriate for lower values of g. Nevertheless, the comparison with the Monte Carlo calculations shows that the model of eq. (32) yields good results, especially in the fluorescence lineshape, which should permit lineshape extraction methods to be developed from a measurement of the fluorescence and reflectance.

Figure 14A:
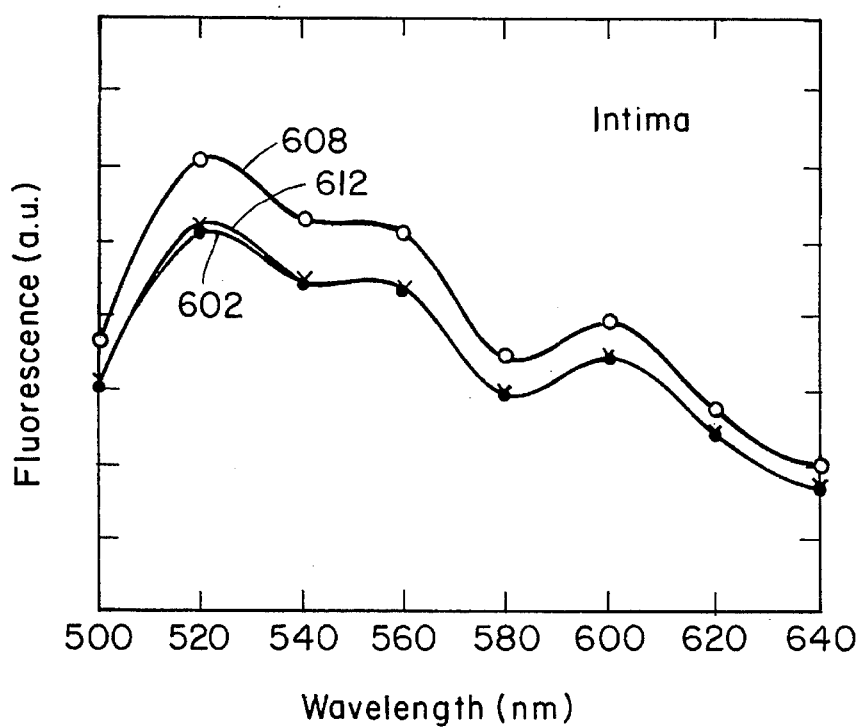
FIGS. 14(a) and 14(b) show shows a comparison of diffusion theory models with Monte Carlo for (a) intima and (b) media. The solid circles are from Monte Carlo simulations, the open circles and sold squares are from diffusion theory, Eddington approximation and delta-Eddington approximation, respectively. The lines are cubic spline curve fits.
Figure 14B:
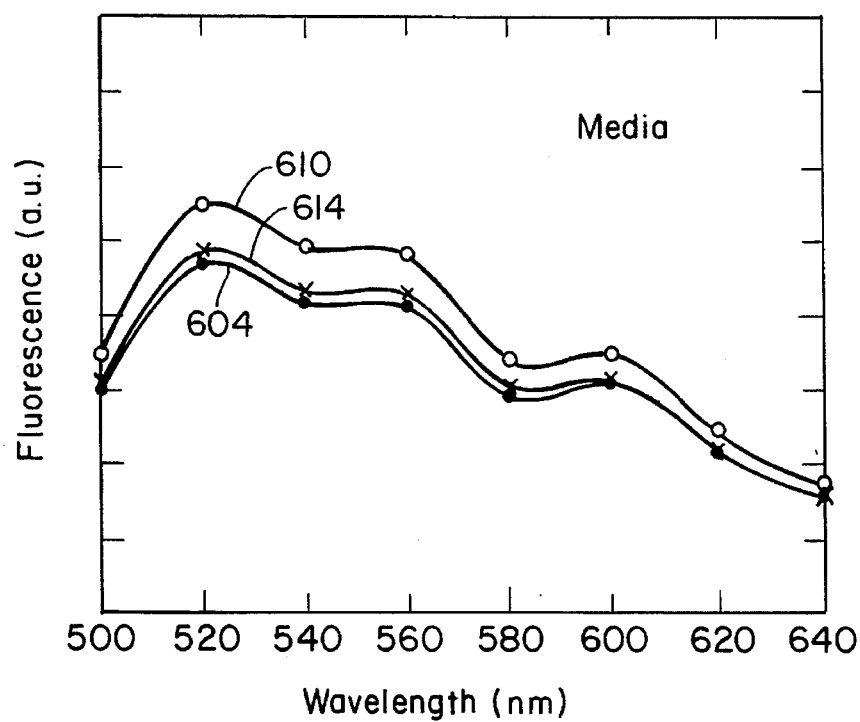

FIGS. 14(a) and 14(b) show the comparison of the Monte Carlo 602, 604 simulations with the Eddington 608, 610 and delta-Eddington 612, 614 approximations of diffusion theory. The delta-Eddington approximation provides the best overall fit to the simulations, because it deals with the highly anisotropic scattering events and the isotropic fluorescence events separately and accurately. However, as stated earlier, neither of these approximations can provide a simple method for extracting the intrinsic fluorescence of the tissue, as required for development of a diagnostic method based on the biochemical or morphological tissue properties.

Fluorescence/Reflectance Experiments

In order to test eq. (34) experimentally, fluorescence and diffuse reflectance spectra from human aortic media were collected utilizing a Spex spectrofluorimeter. This instrument focuses the beam to a 2 mm spot on the tissue, and collects the fluorescence light in a small solid angle at 23° with respect to the tissue surface normal direction. The tissue specimens were collected at autopsy within 24 hours of death. Upon receipt, samples were snap frozen in liquid nitrogen/isopentane and stored at −70° C. until the experiments. At the time of experiments, specimens were passively thawed to room temperature, and were kept moist in a buffered isotonic saline solution. The intima layer was removed before obtaining spectra.

Tissue samples were placed in a quartz cuvette with saline, and the lumen side was oriented towards the window to be irradiated. The quartz material was assumed to be index-matched with the tissue, and the tissue-quartz-air boundary was simplified as a tissueair boundary with the relative refractive indices of 1.4. Bulk fluorescence, $F(\lambda_m)$ in eq. (34), was obtained with 476 nm excitation, and the emission was measured from 500 nm to 650 nm in 2 nm intervals. Diffuse reflectance, $R(a(\lambda),g)$, was measured from 450 nm to 650 nm in 2 nm intervals. Reflectance from a cuvette of $BaSO_4$ powder was also measured and used as the reflectance standard. Both the fluorescence and the reflectance experiments were carried out in the exact same geometry. $R(a(\lambda),g)$ was changed to $R(a_{eff}(\lambda_m),g_{eff})$ using eq. (35) utilizing aorta tissue parameters, g and $\mu_s$, from the literature. In order to test the effect on the technique of changing the absorption coefficient, the aortic media was soaked for various times in diluted lysed whole blood. The resulting fluorescence spectra showed the effect of reabsorption of the fluorescence light from the oxyhemoglobin, as discussed below.

After the bulk fluorescence and diffuse reflectance spectra were obtained, the specimens were frozen again in liquid nitrogen and mounted on microtome chucks. 10 µm thick sections were cut and placed on glass slides, covered with a drop of saline and by glass cover slips to keep the tissue slices moist. The intrinsic fluorescence lineshape, $\phi(\lambda_m)$, was measured from the 10 µm sections for comparison to that obtained using eq. (34).

Figure 15:
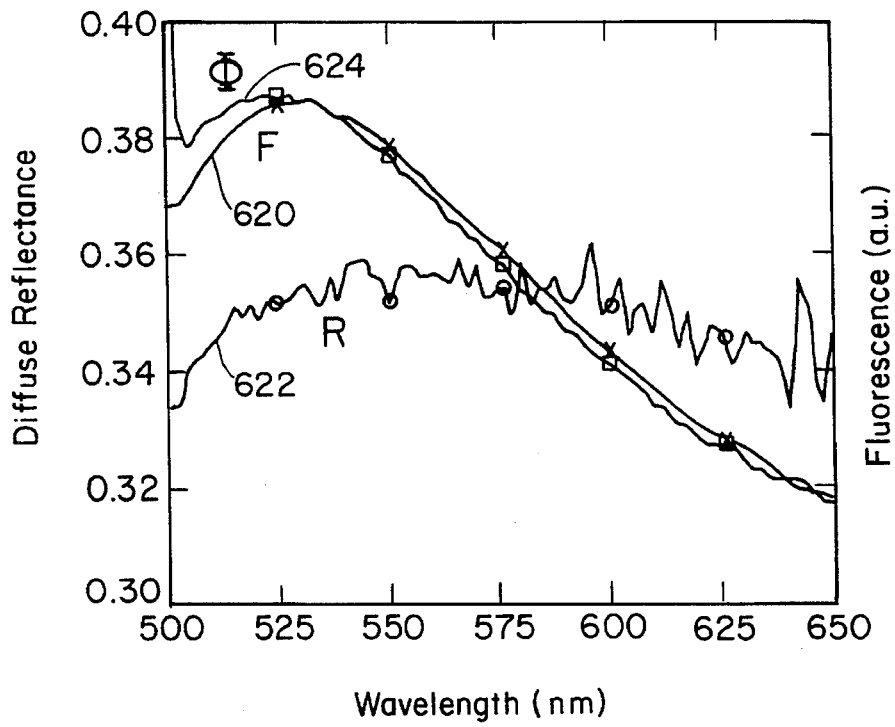
FIGS. 15(a) and 15(b) show experimental data from human aortic media soaked in saline. (a) Comparison of optically thick fluorescence (crosses), reflectance spectrum (circles) and thin fluorescence (squares). (b) Comparison of the intrinsic fluorescence extracted using the model (crosses) and measured from thin sample (squares), include residuals (circles).
Figure 15:
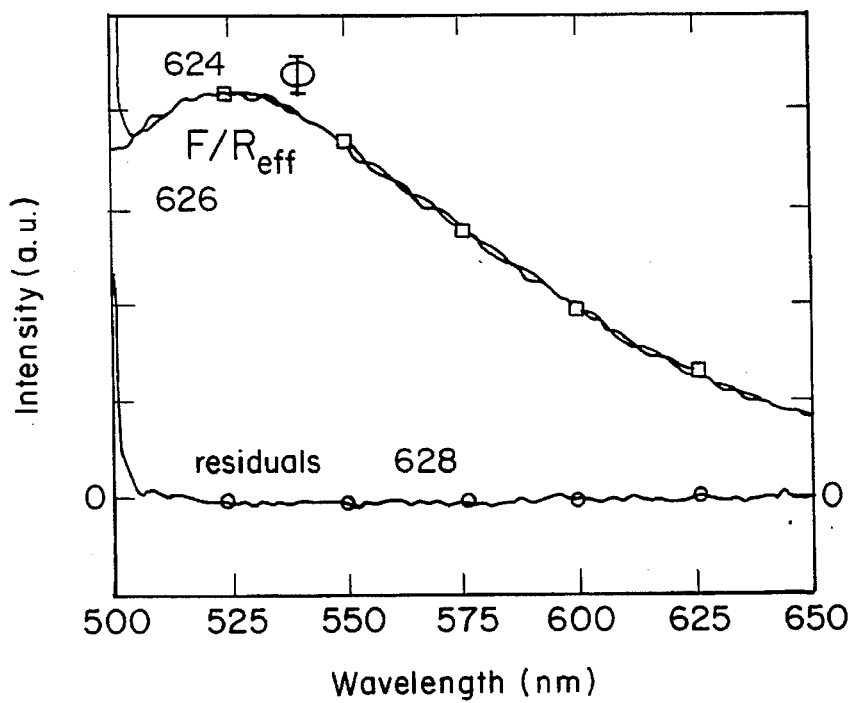

FIG. 15(a) compare the fluorescence 620 and diffuse reflectance 622 spectra observed from optically thick aortic media soaked in saline, and the intrinsic fluorescence spectrum 624 measured from a 10 µm section of media. The bulk tissue fluorescence spectra show the typical lineshape expected from the elastin rich media, and the reflectance matches previously reported data. When the fluorescence spectrum 620 is divided by the effective reflectance spectrum according to eq. (34), the curve 626 maximum shifts slightly to shorter wavelength, as shown in FIG. 15b. Also shown in FIG. 15b is the intrinsic fluorescence spectrum 624. Both spectra are normalized to the same integrated intensity for comparison; the match is remarkable, as can be seen from the calculated residuals 628, also shown in this figure.

Figure 16A:
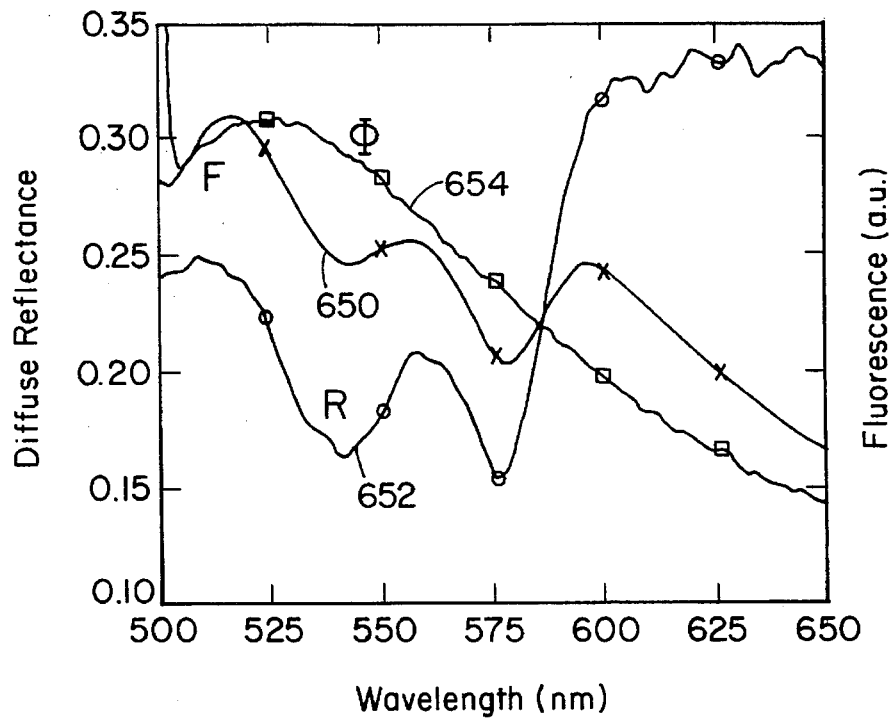
FIGS. 16(a) and 16(b) show experimental data from human aortic media soaked in lysed blood. (a) Comparison of optically thick fluorescence (crosses), reflectance spectrum (circles) and thin fluorescence (squares). (b) Comparison of the intrinsic fluorescence extracted using the model (crosses) and measured from thin sample (squares), include residuals (circles).
Figure 16B:
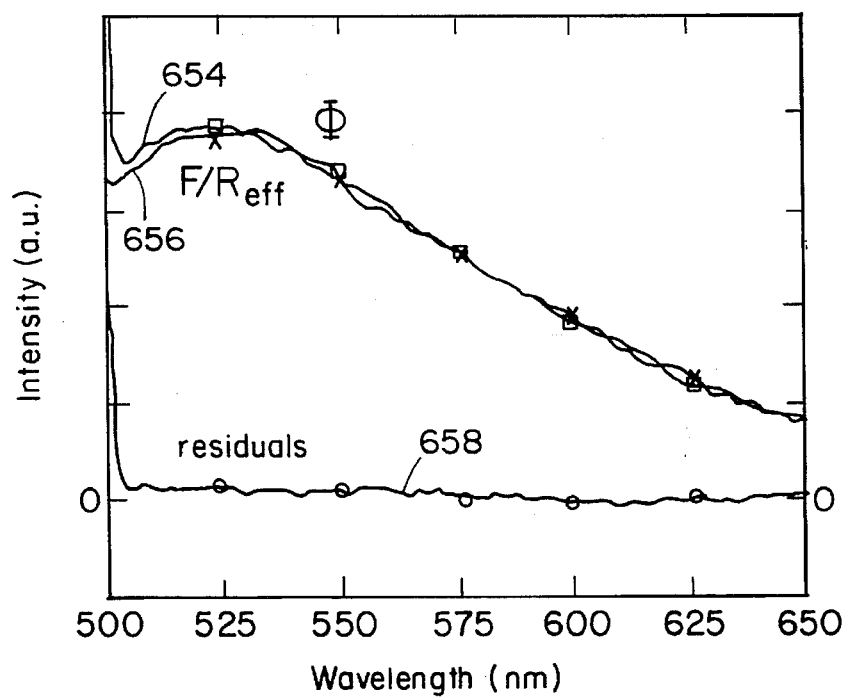

FIG. 16(a) compares the fluorescence 650 and diffuse reflectance 652 spectra obtained from optically thick aorta media which had been soaked overnight in diluted lysed whole blood. The two valleys in the fluorescence spectrum at 540 nm and 580 nm are due to absorption of the emission light by the oxy-hemoglobin. The resulting bulk fluorescence spectrum is heavily distorted from the intrinsic fluorescence 654 of the system. However, the effect of the hemoglobin is removed from the spectrum using eq. (34), as shown in FIG. 16(b). Here, the intrinsic fluorescence 654 measured from a 10 µm section again matches very well with that calculated 656 using eq. (34). This technique has effectively removed the effects of attenuation (absorption and scattering) from the observed signal of the bulk tissue spectrum, allowing the intrinsic fluorescence spectrum to be extracted.

The result of the photon migration approach to tissue fluorescence is that by measuring the diffuse reflectance spectrum over the same wavelength range and in the same geometrical configuration as the bulk fluorescence spectrum, an intrinsic fluorescence lineshape can be extracted which is undistorted by the scattering and absorption in the tissue. Thus, the distortion of the fluorescence lineshape associated with the absorption and scattering of the excitation and emission light, and geometry of irradiation and collection, and boundary conditions can be removed. This provides significant correlation between the in vivo microspectroscopy experiment on thin tissue sections and in vivo clinical data, despite the fact that these two types of experiments were performed in different geometrics. Since, ultimately, microspectroscopy provides the fluorescence lineshapes of the individual morphological structures, $\phi(\lambda_m)$, one can then deconvolve the contribution of each of the morphological structures using the simple relation:

$$\phi(\lambda_m) = \sum_i c_i' \frac{(\mu_a)_i}{\mu_a} \quad \phi_i(\lambda_m) = \sum_i c_i \phi_i(\lambda_m) \tag{36}$$

where $c_i$ is proportional to the individual chromophore concentration, and can be obtained by fitting the experimental data to eq. (36).

As discussed earlier, eq. (34) is valid over a range where $\mu_s(1-g)$ is less than 10 times greater than $\mu_a$, i.e. the range over which eq. (28) is valid. In addition, since-in(a) was expanded to (1-a) in order to obtain eq. (33), eq. (34) becomes invalid for large values of $\mu_a$. It has been found that when the measured reflectance at the hemoglobin absorption valley was less than 5%, eq. (34) could not completely remove the distortions from the fluorescence spectrum. In this case, the albedo should be evaluated first from the reflectance by using the $f_n$ curve in the given geometry and boundary condition, and then eq. (32) should be utilized. In addition, the photon migration model is derived under the condition that the tissue fluorophores and absorbers are assumed to be homogeneously distributed. The situation can be quite different when the tissue consists of several layers in which the optical parameters are very disparate. This methodology is readily adapted to handle multi-layered tissues, where each layer would exhibit it own characteristic $M_a$, $M_s$, and g parameters. Multiple boundary conditions would also typically exist between the multiple layers due to differing indices of refraction.

The method for extracting intrinsic fluorescence presented herein can be related to another development method, in which the bulk fluorescence, $F(\lambda_m)$, is given by:

$$F(\lambda_m) = \frac{k\mu_a \phi(\lambda_m)}{A(\lambda_x, \lambda_m)} \quad (37)$$

with $\mu_a$ and $\phi$ as defined above, k a constant determined by geometry and relative refractive indices, and A an attenuation lineshape which incorporates the net effect of absorption and scattering. Equation (37) provides the basis for a curve fitting approach in which the intrinsic fluorescence can be extracted from F in an experimental arrangement in which the light delivery and collection are fixed. This approach was applied to the diagnosis of artery wall tissue. A fiber optic catheter probe with fixed delivery and collection geometry was employed. The lineshapes for $\phi$ and A were expressed as linear combinations of spectral components corresponding to constituent tissue chromophores. Using eq. (37), the attenuation A was then evaluated by measuring fluorescence from both optically thick and thin samples of known composition. The observed fluorescence lineshape, F, from an unknown artery sample could then be fit to eq. (37), and an accurate tissue diagnosis could be made from the resulting fit coefficients.

The procedure for extracting intrinsic fluorescence is consistent with that of eq. (34), provided A is identified with $\mu_a/R_{eff}$. The success of the curve fitting approach of eq. (37) in extracting $\phi$ can thus be considered as additional support for the validity of eq. (34). Equation (34) is, of course, more generally applicable, because it also provides a method of extracting the intrinsic fluorescence directly from the experimental determination of F and R, even in situations in which the geometry is not fixed and/or the knowledge of the attenuation is incomplete. However, the curve fitting procedure provides an alternative method for extracting $\phi$ in cases where the reflectance information is not readily available.

Another important feature of this technique resulting from the photon migration model of tissue fluorescence is that it can be readily applied in the clinical setting. Clinical apparatus which are used to measure fluorescence can be easily modified for the determination of the diffuse reflectance. Only a common white light source and a beam splitter need to be added to the light delivering subsystem to determine the reflectance. However, one must avoid the specular reflectance that may return through a fiber optical probe, or careful subtraction of the specular component must be carried out.

In addition to its application to human tissue fluorescence, the methodology presented here has broader applications. Studies of fluorescence in other turbid situations, such as binding to large polymers of DNA or whole cells, would benefit from measuring the reflectance and applying eq. (34). Similarly, this approach can be used to model the Raman scattering spectroscopy from human tissue or other turbid situations (R. P. Rava, J. J. Baraga and M. S. Feld, "Near, infrared Fourier transform Raman spectroscopy of human artery," Spectrochim Acta 47A, 509–512 (1991)). In the Raman case, an infrared source, such as a glow bar or other infrared emitting heat source, is used to induce Raman spectral emissions from the tissue sample which is measured as the bulk Raman spectrum. here, the intrinsic Raman spectrum is related to the measured diffuse reflectance spectrum and the measured bulk Raman spectrum by a proportion constant different from the fluorescence case. That is, the product of the Raman cross section times the density, $\rho\sigma_{Raman}\mu_t(\lambda_x)$, replaces the term $(1-a(\lambda_x))\phi(\lambda_x,\lambda_m)$ in eq. (29). Because Raman scattering is highly forward directed, the use of the effective anisotropy coefficient, $g_{eff}$, is not necessary, and thus, it is expected that the present model will work even better for Raman spectroscopy than for fluorescence.

A model of fluorescence from human tissue based on the photon migration theory has thus been presented, which can be used to extract the intrinsic fluorescence spectrum from the optically thick tissue fluorescence spectrum even when the latter has been distorted by the interplay of tissue scattering, absorption, refractive index, excitation and collection geometry. The validity of this technique has been verified by both Monte Carlo simulations and laboratory experiments. It has been demonstrated that by measuring the diffuse reflectance spectrum over the same wavelength range as the fluorescence spectrum, the intrinsic tissue fluorescence spectrum can be easily obtained to provide useful information of the tissue fluorophores.

While this invention has been particularly shown and described with references to preferred embodiments thereof, it will be understood by those skilled in the art that various changes in form and details may be made therein without departing from the spirit and scope of the invention as defined by the appended claims.

One-Dimensional Diffusion Calculation for Fluorescence

For a semi-infinite one-dimensional slab, the tissue fluorescence can be calculated within diffusion theory using the Eddington approximation. The problem can be broken into two parre: i) determination of the incident light distribution within tissue excited by a plane wave incident on a slab; and ii) determination of the diffusion from a point source within the tissue.

For a plane wave of flux density $F_o$ (mW mm$^{-2}$ Hz$^{-1}$) incident on a slab of tissue, the specific intensity at a depth z in the tissue, $I(z, \omega)$ (mW mm$^{-2}$ sr$^{-1}$ Hz$^{-1}$), can be divided into two pans, the reduced incident intensity, $I_{ri}(z, \omega)$, and the diffuse intensity, $I_d$. $I_{ri}(z, \omega)$ is given by $$I_{ri}(z, \omega) = F_o \exp(-\mu_t z)\delta(\omega - \omega_z) \quad (A.1)$$

where $\mu_t$ (mm$^{-1}$) is the total anenuaxion coefficient given by the sum of the scanrang coefficient, $\mu_s$, and the absorption coefficient, $\mu_a$; and $\delta(\omega-\omega_z)$ (sr$^{-1}$) is the solid angle delta function. The diffuse intensity component is obtained by solving the diffusion equation which for this case is $$\frac{d^2 U_d(z)}{dz^2} - \kappa_d^2 U_d(z) = Q_o \exp(-\mu_t z) \quad (A.2)$$

In eq. A.2, the average diffuse intensity, $$U_d(z)(mW\, mm^{-2}\, Hz^{-1}) = \frac{1}{4\pi} \int_{4\pi} I_d d\omega (mW\, mm^{-2}\, Hz^{-1});$$

$$Q_o = \frac{3F_o(\mu_s\mu_\pi + g\mu_s\mu_t)}{4\pi}$$

and $$\kappa_d = \sqrt{3\mu_{tr}\mu_a}\ .$$

The anisotropy coefficient, g, describes the phase dependence of the scattering and $\mu_{tr}\mu_s(1-g)+\mu_a$. Under indexmatched boundary conditions $$U_d(z) - h \frac{dU_d(z)}{dz} + \frac{Q_1}{2\pi} = 0 \text{ at } z = 0 \quad (A.3)$$

$$U_d(z) = 0 \text{ at } z = +\infty$$

where $$h = \frac{2}{3\mu_{tr}}$$

and $$Q_l = \frac{\mu_s g}{\mu_{tr}} F_o,$$

the solution for $U_d(z)$ is:

$$U_d(z) = A\exp(-\mu_t z) + C_2 \exp(-\kappa_d z) \quad (A.4)$$

where where $$A = \frac{Q_o}{(\mu_t^2 - \kappa_k^2)}$$

and $$C_2 = \frac{-A(1 + \mu_t h)}{1 + \kappa_d h} - \frac{Q_l}{2\pi(1 + \kappa_d h)}.$$

Thus the total intensity at depth z is given by $$I_{total}(z) = 4\pi U_d(z) + I_{ri}(z) \quad (A.5)$$

Now that the intensity of the incident light at depth z within the tissue is known, we need to determine the fluorescence intensity that returns upwards back to the tissue surface for detection. In this problem, we are considering diffusion from a uniform layer of point (fluorescence) sources within the tissue. The position of the some hyer is considered to be at z=0, with the z axis increasing upwards towards the tissue surface, where $z=z_o$. The diffusion equation for this situation is:

$$\frac{d^2 U_d(z)}{dz^2} - \kappa_d^2 U_d(z) = \frac{-3}{4\pi} \mu_{tr} P_o \delta(z=0) \quad (A.6)$$

with the boundary conditions:

$$U_d(z) + h \frac{dU_d(z)}{dz} = 0 \text{ at } z = z_o \quad (A.7)$$

-continued $$U_d(z) = 0 \text{ at } z = -\infty$$

The solution is found to be:

$$U_d(z) = B \exp(\kappa_d z) + \frac{3P_o}{8\pi} \frac{\mu_{tr}}{\kappa_d} \exp(-\kappa_d z), 0 < z < z_o \quad (A.8)$$

where $$B = \frac{P_o}{4\pi} \exp(-2\kappa_d z_o) \frac{1 - 3\mu_{tr}/2\kappa_d}{1 + 2\kappa_d/3\mu_{tr}}.$$

The total flux emitted at the surface ($z=z_o$) can be calculated from:

$$F_d = \frac{-4\pi}{3\mu_{tr}} \frac{dU_d(z)}{dz} = CP_o \exp(-\kappa_d z_o) \quad (A.9)$$

with $$C = \frac{3\mu_{tr}}{3\mu_{tr} + 2\kappa_d}.$$

The observed fluorescence can now be calculated as:

(A.10)

$$F(\lambda_x, \lambda_m) = \int_0^{+\infty} dz \{[(4\pi A(\lambda_x) + F_o)\exp(-\mu_t(\lambda_x)z) + 4\pi C_2(\lambda_x)\exp(-\kappa_d(\lambda_x)z)]$$
$$\mu_a(\lambda_x)\phi(\lambda_x, \lambda_m) C(\lambda_m) \exp(-\kappa 1 d(\lambda_m)z)\}$$
$$= \mu_a(\lambda_x)\phi(\lambda_x, \lambda_m) \left\{ \frac{4\pi A(\lambda_x) + F_o}{\mu_t(\lambda_x) + \kappa_d(\lambda_m)} + \frac{4\pi C_2(\lambda_x)}{\kappa_d(\lambda_x) + \kappa_d(\lambda_m)} \right\} C(\lambda_m)$$

where $\lambda_x$ and $\lambda_m$ are the excitation and emission wavelengths, respectively. The solution of the delta-Eddington approximation[15] is also given by eq. (A.10), with $\mu_a$, $\mu_s$, and g replaced by $\mu_a' = \mu_a, \mu_s' = (1-g^2)\mu_s, g' = g/(1+g)$.

We claim:

1. A spectroscopic method of analyzing tissue, comprising:

illuminating a region of tissue with a first light source to induce an inelastically scattering emission from the tissue in a range of wavelengths;

illuminating the region of tissue with a second white light source to induce diffuse reflectance of light from the tissue;

collecting inelastically scattering radiation emitted from the tissue at the wavelengths in the range of wavelengths;

collecting diffuse reflectance radiation emitted from the tissue at the wavelengths within the range of wavelengths of the inelastically scattering emission;

coupling the collected inelastically scattering and diffuse reflectance emissions to a spectral analyzer; and determining intrinsic inelastic scattering of the tissue at each wavelength within the range of wavelengths by adjusting the collected inelastically scattering radiation at each wavelength with the collected diffuse reflectance at the same wavelength.

2. The method of claim 1 wherein, the step of collecting inelastically scattering radiation comprises collecting fluorescence emission.

3. The method of claim 2, further comprising the steps of deconvolving the intrinsic fluorescence spectrum with a plurality of known fluorophoric lineshapes to determine the best lineshape fit to the intrinsic fluorescence spectrum;

determining the presence and concentration of the known fluorophoric elements from the best fit lineshape; and diagnosing the tissue from the determined fluorophoric element concentrations.

4. The method of claim 2, wherein the determining step comprises generating an approximation of an intrinsic fluorescence spectrum $\phi(\lambda_m)$ of the tissue which is proportional to a measured bulk fluorescence $F(\lambda_m)$ divided by an effective form $R_{eff}$ of a measured diffuse reflectance R.

5. The method of claim 4, wherein the effective reflectance $R_{eff}$ is related to the measured reflectance R by the relationship $$\frac{\frac{1}{R_{eff}} - 1}{\frac{1}{R} - 1} \approx \frac{1-g}{1-g_{eff}} \left( r_d + (1 - r_d) \frac{\mu_s^2(\lambda_m)}{\mu_s^2(\lambda_x)} \right)$$

where g is the anisotropy coefficient, $g_{eff}$ is the effective anisotropy coefficient, $r_d$ is the probability of a photon being internally reflected at a tissue boundary, and, $\mu_s(\lambda_m)$ and $\mu_s(\lambda_x)$ are the scattering coefficients for the incident and fluorescence wavelengths, respectively.

6. The method of claim 5, wherein $r_d$ is equal to about 0 for index-matched boundary conditions.

7. The method of claim 5, wherein $r_d$ is equal to about 0.53 for index-mismatched boundary conditions and refractive indices of about 1.4.

8. The method of claim 5 wherein $\mu_s(\lambda_x)$ and $\mu_s(\mu_m)$ are within the range of 0.1 mm$^{-1}$ to 2.0 mm$^{-1}$, and g is _ _ , within the range of 0.68 to 0.96.

9. The method of claim 2, wherein the step of illuminating a reqion of tissueswith a first light source comprises illuminating the region of tissue with substantially monochromatic light.

10. The method of claim 9, wherein the step of illuminating a region of tissue with a first light source includes activating a tunable laser.

11. The method of claim 9, wherein the step of illuminating a region of tissue with a first light source includes activating a white light source or a monochromator.

12. The method of claim 9, wherein the step of illuminating a reqion of tissue with a first light source includes activating a laser.

13. The methods of claim 9, wherein the step of illuminating a reqion of tissue with a first light source includes illuminating the tissue with monochromatic light having a wavelength of substantially 476 nm.

14. The method of claim 2, wherein the step of illuminating the region of tissue with a second white light source includes scanning a tunable laser over a band of wavelengths.

15. The method of claim 2, wherein the step of illuminating the region of tissue with a second white light source includes illuminating the tissue with light having wavelengths of substantially 450–650 nm.

16. The method of claim 1, wherein the step of collecting inelastically scattering radiation comprises collecting Raman emission.

17. The method of claim 16, wherein the step of illuminating a region of tissue with a first light source comprises generating infrared light.

18. The method of claim 1 further comprising forming a simulated representation of reflectance of radiation from the tissue and comparing the representation with the collected reflectance emission.

19. The method of claim 18 wherein the step of forming a simulated representation comprises performing a Monte Carlo simulation.

20. The method of claim 1 further comprising inserting a catheter or endoscope into a bodily vascular lumen, illuminating material within the vascular lumen with light from the first source and light from the second light source through the fiber optic catheter or endoscope and collecting radiation returning from the tissue with the catheter or endoscope.

21. A spectroscopic method of analyzing tissue, comprising inserting a fiber optic probe into a body lumen;

illuminating a region of tissue with a first light source through the fiber optic probe to induce an inelastically scattering emission from the tissue;

illuminating the region of tissue with a second light source through the fiber optic probe to induce diffuse reflectance of light from the tissue;

collecting inelastically scattering radiation returning from the tissue through the fiber optic probe at a plurality of wavelengths;

collecting diffuse reflectance radiation returning from the tissue through the fiber optic probe at the same plurality of wavelengths, the collected diffuse reflectance having been induced at the plurality of wavelengths upon illumination of the tissue with the second light source;

coupling the collected inelastically scattering and diffuse reflectance radiation from the fiber optic probe to a spectral analyzer; and determining intrinsic inelastic scattering of the tissue at the plurality of radiation by adjusting the collected inelastically scattered wavelength at each wavelength with the collected diffuse reflectance at the same wavelength.

22. The method of claim 21 further comprising determining whether the tissue is cancerous, pre-cancerous or non-cancerous.

* * * * *